US011382715B2

(12) United States Patent
Arai et al.

(10) Patent No.: US 11,382,715 B2
(45) Date of Patent: Jul. 12, 2022

(54) JIG-HOLDING DEVICE AND MEDICAL OBSERVATION DEVICE

(71) Applicant: SONY CORPORATION, Tokyo (JP)

(72) Inventors: Jun Arai, Kanagawa (JP); Yohei Kuroda, Tokyo (JP); Yasuhisa Kamikawa, Tokyo (JP); Wataru Kokubo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 876 days.

(21) Appl. No.: 16/087,152

(22) PCT Filed: Feb. 6, 2017

(86) PCT No.: PCT/JP2017/004154
§ 371 (c)(1),
(2) Date: Sep. 21, 2018

(87) PCT Pub. No.: WO2017/169118
PCT Pub. Date: Oct. 5, 2017

(65) Prior Publication Data
US 2019/0099238 A1    Apr. 4, 2019

(30) Foreign Application Priority Data
Mar. 31, 2016    (JP) .............................. JP2016-070594

(51) Int. Cl.
*A61B 90/50*        (2016.01)
*A61B 1/00*         (2006.01)
(52) U.S. Cl.
CPC .......... *A61B 90/50* (2016.02); *A61B 1/00128* (2013.01); *A61B 1/00133* (2013.01); *A61B 1/00149* (2013.01); *A61B 1/00066* (2013.01); *A61B 1/00112* (2013.01)
(58) Field of Classification Search
CPC . A61B 90/50; A61B 1/00131; A61B 1/00133; A61B 1/00147; A61B 1/00149; A61B 1/00112; A61B 1/00128; A61B 1/00066
See application file for complete search history.

(56) References Cited

U.S. PATENT DOCUMENTS

2014/0166023 A1    6/2014    Kishi

FOREIGN PATENT DOCUMENTS

| JP | 63-270033 A | 11/1988 |
|---|---|---|
| JP | 64-25833 A | 1/1989 |
| JP | 5-82998 A | 4/1993 |
| JP | 10-210776 A | 8/1998 |
| JP | 2000-60159 A | 2/2000 |
| JP | 2013-34833 A | 2/2013 |

OTHER PUBLICATIONS

International Search Report dated Apr. 25, 2017 in PCT/JP2017/004154, 2 pages.

*Primary Examiner* — Katherine M Rodjom
(74) *Attorney, Agent, or Firm* — Xsensus, LLP

(57) ABSTRACT

To provide a jig holding apparatus and medical observation apparatus, which enable linear motion of a jig without increasing the size of a holding mechanism configured to hold the jig. A jig holding apparatus (1) includes: a holding mechanism (100) including a holding section (173) configured to detachably hold a predetermined jig (10) from a periphery of the jig (10), and a linear motion driving section (130) provided around the jig (10) held by the holding section (173) and configured to cause the jig (10) to linearly move.

18 Claims, 15 Drawing Sheets

JIG-HOLDING DEVICE AND MEDICAL OBSERVATION DEVICE

TECHNICAL FIELD

The present disclosure relates to a jig-holding apparatus and a medical observation apparatus.

BACKGROUND ART

Conventionally, miniaturization of a holding mechanism or holding apparatus for holding various surgical jigs such as an endoscope, forceps, or retractor has been desired in order to secure a field of view or a workspace of a doctor during surgery or to prevent the arrangement of numerous instruments in an operating room from being impeded. An example of the holding apparatus may include a support arm apparatus which has a holding mechanism, which is configured to hold a jig, formed at a front end section. An example of the holding mechanism may include a holding mechanism which has a hollow shape and is configured to hold a jig at a hollow portion.

Here, an actuator or a brake mechanism is required to cause a jig to move to a position desired by the doctor and cause the jig to be held at that position during surgery. When such an actuator or brake mechanism is provided on the holding mechanism, there is a concern that the size of the holding mechanism will be increased. In contrast, Patent Literature 1 discloses an ultrasonic endoscope in which an ultrasonic vibrator provided at a front end of an insertion part is attached to a front end section of a rotating shaft which is caused to extend inside the insertion part so that the rotating shaft is caused to rotate to scan-drive the ultrasonic vibrator, in which the rotating shaft is configured to be rotated by an ultrasonic motor disposed concentrically with the rotating shaft.

CITATION LIST

Patent Literature

Patent Literature 1: JP S63-270033A

DISCLOSURE OF INVENTION

Technical Problem

However, the ultrasonic endoscope described in Patent Literature 1 is intentionally configured as an endoscope of a type which is hand-held and operated by a doctor. For this reason, it is assumed that a linear motion operation in an axial direction of a rotation axis is performed by a doctor, and a driving section for causing the linear motion operation to be performed is not provided. In a case in which a jig is caused to be held by a holding apparatus such as a support arm apparatus, although a large linear motion operation can be caused to be performed by controlling the attitude of the arm, it is considered to be more efficient if a small linear motion operation can be caused to be performed without causing the attitude of the arm to be changed.

Accordingly, the present disclosure proposes a novel and improved jig holding apparatus and medical observation apparatus, which enable linear motion of a jig without increasing the size of a holding mechanism configured to hold the jig.

Solution to Problem

According to the present disclosure, there is provided a jig holding apparatus including: a holding mechanism including a holding section configured to detachably hold a predetermined jig from a periphery of the jig, and a linear motion driving section provided around the jig held by the holding section and configured to cause the jig to linearly move.

According to the present disclosure, there is provided a medical observation apparatus including a holding mechanism having an endoscope, a holding section configured to detachably hold the endoscope, and a linear motion driving section provided around the holding section and configured to cause the endoscope to linearly move.

Advantageous Effects of Invention

According to the present disclosure, as described above, linear motion of a jig can be enabled without increasing a size of a holding mechanism configured to hold the jig. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
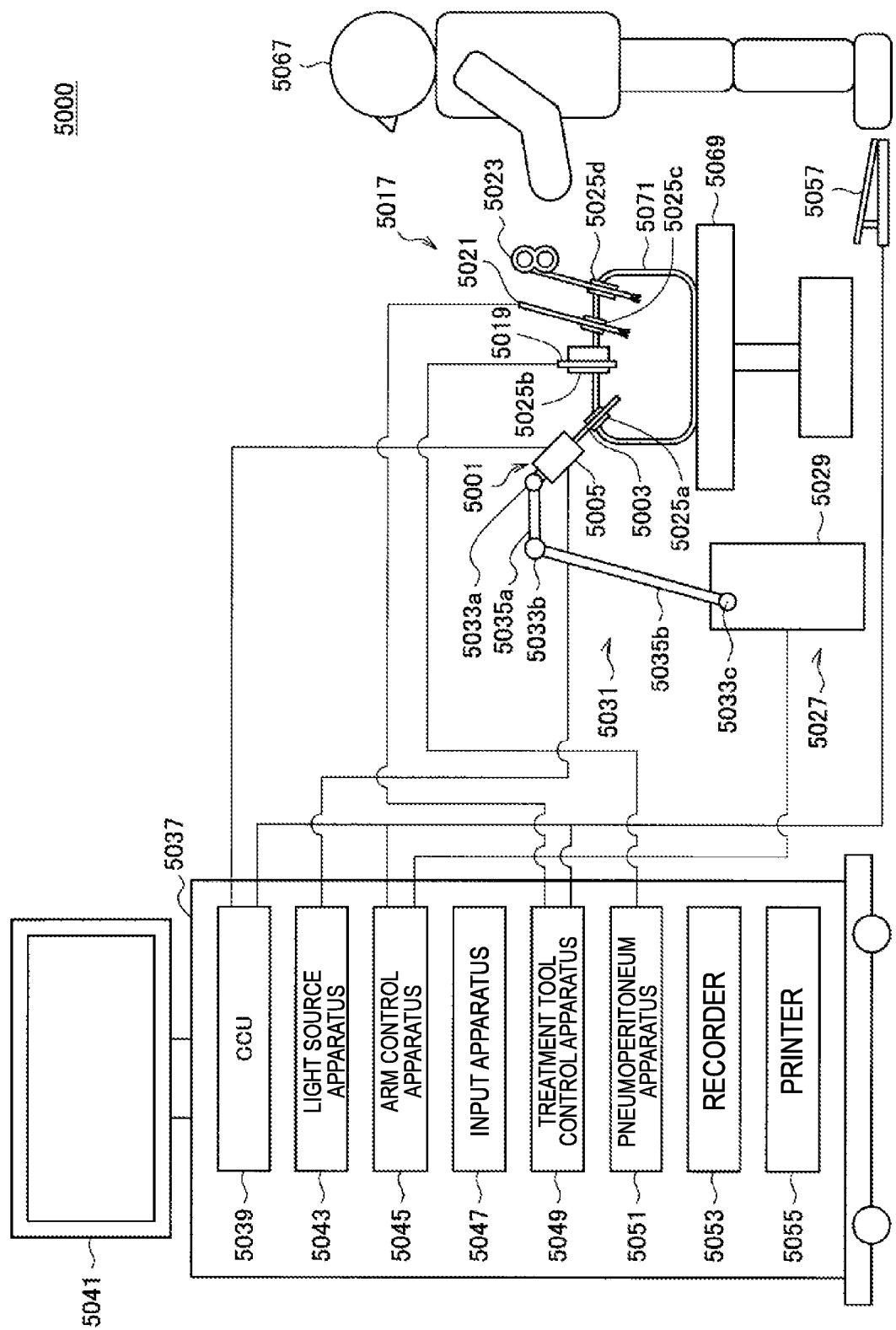
FIG. 1 is a diagram illustrating an example of a schematic configuration of an endoscopic surgery system to which a jig holding apparatus of the present disclosure is applicable.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.
1. Basic configuration of endoscopic surgery system
1-1. Support arm apparatus (jig holding apparatus)
1-2. Endoscope
1-3. Various apparatuses provided on cart
1-4. Specific configuration of support arm apparatus
1-5. Light source apparatus
1-6. Camera head and CCU
2. First embodiment (example in which ultrasonic motor is used)
2-1. Basic configuration of holding mechanism
2-2. Rotating driving section
2-3. Linear motion driving section
2-4. Clean area and unclean area
2-5. Positioning mechanism
2-6. Expansion of workspace
3. Second embodiment (example in which electromagnetic motor is used)
3-1. Rotation driving section
3-2. Linear motion driving section

1. Basic Configuration of Endoscopic Surgery System

First, among configurations of an endoscopic surgery system to which the technology according to the present disclosure is applicable, a basic configuration which is common to each embodiment which will be described below will be described.

FIG. 1 is a diagram illustrating an example of a schematic configuration of an endoscopic surgery system 5000 to which the technology according to the present disclosure may be applied. FIG. 1 illustrates a situation in which a surgeon (doctor) 5067 is using an endoscopic surgery system 5000 to perform surgery on a patient 5071 lying on a patient bed 5069. As illustrated in the diagram, the endoscopic surgery system 5000 includes an endoscope 5001, other surgical instruments 5017, a support arm apparatus 5027 that supports the endoscope 5001, and a cart 5037 on which various apparatus for endoscopic surgery are provided.

In endoscopic surgery, instead of opening up the abdomen by cutting the abdominal wall, tubular hole-opening tools called trocars 5025a to 5025d are used to puncture the abdominal wall in multiple places. Subsequently, the lens tube 5003 of the endoscope 5001 and other surgical instruments 5017 are inserted into the body cavity of the patient 5071 from the trocars 5025a to 5025d. In the illustrated example, a pneumoperitoneum tube 5019, an energy treatment tool 5021, and forceps 5023 are inserted into the body cavity of the patient 5071 as the other surgical instruments 5017. Further, the energy treatment tool 5021 is a treatment tool that makes incisions into and ablates tissues, or seals blood vessels or the like, with a high-frequency electric current or ultrasonic vibration. However, the surgical instruments 5017 illustrated in the diagram are merely an example, and any of various types of surgical instruments typically used in endoscopic surgery, such as tweezers and retractors, for example, may also be used as the surgical instruments 5017.

An image of the operating site inside the body cavity of the patient 5071 taken by the endoscope 5001 is displayed on a display apparatus 5041. The surgeon 5067 uses the energy treatment tool 5021 and the forceps 5023 to perform treatments, such as excising an affected area, for example, while watching in real time the image of the operating site displayed on the display apparatus 5041. Note that, although omitted from the diagram, the pneumoperitoneum tube 5019, the energy treatment tool 5021, and the forceps 5023 are supported by a person such as the surgeon 5067 or an assistant during surgery.

<1-1. Support Arm Apparatus (Jig Holding Apparatus)>

The support arm apparatus 5027 is provided with an arm section 5031 that extends from a base section 5029. In the illustrated example, the arm section 5031 includes joint sections 5033a, 5033b, and 5033c, as well as links 5035a and 5035b, and is driven by a control command from an arm control apparatus 5045. The endoscope 5001 is supported by the arm section 5031, with the position and attitude controlled thereby. With this arrangement, locking of the endoscope 5001 in a stable position may be realized. An endoscope observation apparatus is configured by the endoscope 5001 being supported by the support arm apparatus 5027.

<1-2. Endoscope>

The endoscope 5001 includes a lens tube 5003 having a region of certain length from the front end that is inserted into the body cavity of the patient 5071, and a camera head 5005 connected to the base end of the lens tube 5003. The example illustrates the endoscope 5001 configured as what is called a rigid scope having a rigid lens tube 5003. However, the endoscope 5001 may also be configured as what is called a flexible scope having a flexible lens tube 5003.

On the front end of the lens tube 5003, there is provided an opening into which an objective lens is fitted. A light source apparatus 5043 is connected to the endoscope 5001. Light generated by the light source apparatus 5043 is guided up to the front end of the lens tube 5003 by a light guide extending inside the lens tube 5003, and is radiated through the objective lens towards an observation target inside the body cavity of the patient 5071. Note that the endoscope 5001 may be a forward-viewing scope, and may also be an oblique-viewing scope or a side-viewing scope.

An optical system and an image sensor are provided inside the camera head 5005, and reflected light (observation light) from the observation target is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 5039. Note that the camera head 5005 is provided with a function of adjusting the magnification and the focal length by appropriately driving the optical system.

Note that, to support stereoscopic vision (3D display) or the like, for example, multiple image sensors may be provided in the camera head 5005. In this case, multiple relay optical subsystems are provided inside the lens tube 5003 to guide the observation light to each of the multiple image sensors.

<1-3. Various Apparatus Provided on Cart>

The CCU 5039 includes a central processing unit (CPU), a graphics processing unit (GPU) and the like, and centrally controls the operation of the endoscope 5001 and the display apparatus 5041. Specifically, the CCU 5039 subjects an image signal received from the camera head 5005 to various types of image processing for displaying an image based on the image signal, such as a development process (demosaicing process), for example. The CCU 5039 provides an image signal that has been subjected to such image processing to the display apparatus 5041. Also, the CCU 5039 transmits a control signal to the camera head 5005 to control the driving thereof. The control signal may include information related to imaging conditions, such as the magnification and the focal length.

The display apparatus 5041, under control by the CCU 5039, displays an image based on an image signal subjected to image processing by the CCU 5039. In a case in which the endoscope 5001 supports imaging at a high resolution such as 4K (3840 horizontal pixels×2160 vertical pixels) or 8K (7680 horizontal pixels×4320 vertical pixels), and/or supports 3D display, for example, an apparatus compatible with each and capable of high-resolution display and/or capable of 3D display may be used as the display apparatus 5041. In the case in which imaging at a high resolution such as 4K or 8K is supported, a device with a size of 55 inches or more may be used as the display apparatus 5041 to thereby obtain an even deeper sense of immersion. Also, depending on the application, multiple display apparatus 5041 with different resolutions and sizes may also be provided.

The light source apparatus 5043 includes a light source such as a light-emitting diode (LED), for example, and supplies the endoscope 5001 with irradiating light when imaging the operating site.

The arm control apparatus 5045 includes a processor such as a CPU, for example, and by operating in accordance with a predetermined program, controls the driving of the arm section 5031 of the support arm apparatus 5027 in accordance with a predetermined control method.

The input apparatus 5047 is an input interface with respect to the endoscopic surgery system 5000. Through the input apparatus 5047, the user is able to input various information and instructions into the endoscopic surgery system 5000. For example, through the input apparatus 5047, the user inputs various information related to surgery, such as physical information about the patient, and information about surgical procedures. As another example, through the input apparatus 5047, the user inputs instructions to drive the arm section 5031, instructions to change the imaging conditions of imaging by the endoscope 5001 (such as the type of irradiating light, the magnification, and the focal length), instructions to drive the energy treatment tool 5021, and the like.

The type of the input apparatus 5047 is not limited, and the input apparatus 5047 may be any of various known types of input apparatus. For example, a mouse, a keyboard, a touch panel, a switch, the footswitch 5057, and/or a lever and the like may be applied as the input apparatus 5047. In the case in which a touch panel is used as the input apparatus 5047, the touch panel may be provided on the display screen of the display apparatus 5041.

Alternatively, the input apparatus 5047 is a device worn by the user, such as an eyeglasses-style wearable device or a head-mounted display (HMD), for example, and various types of input is performed in accordance with the user's gestures or gaze, or the like detected by these devices. Further, the input apparatus 5047 includes a camera capable of detecting motions of the user. Various types of input is performed in accordance with the user's gestures or gaze detected from a picture imaged by the camera. Furthermore, the input apparatus 5047 includes a microphone capable of picking up the user's speech. Various types of input is performed by speech through the microphone. In this way, by configuring the input apparatus 5047 to be capable of accepting the input of various types of information in a non-contact manner, a user belonging to a clean area in particular (for example, the surgeon 5067) becomes able to operate equipment belonging to an unclean area in a non-contact manner. Also, since the user becomes able to operate equipment without taking one's hands away from the tools the user is holding, user convenience is improved.

A treatment tool control apparatus 5049 controls the driving of the energy treatment tool 5021 to cauterize or make incisions into tissue, seal blood vessels, or the like. A pneumoperitoneum apparatus 5051 delivers gas into the body cavity through the pneumoperitoneum tube 5019 to inflate the body cavity of the patient 5071 for the purpose of securing a field of view for the endoscope 5001 and securing a workspace for the surgeon. A recorder 5053 is an apparatus capable of recording various types of information related to surgery. A printer 5055 is an apparatus capable of printing out various types of information related to surgery in various formats, such as text, images, or graphs.

Hereinafter, the characteristic configuration in particular in the endoscopic surgery system 5000 will be described in further detail.

<1-4. Specific Configuration of Support Arm Apparatus (Jig Holding Apparatus)>

The support arm apparatus 5027 is provided with a base section 5029 which acts as a base, and the arm section 5031 which extends from the base section 5029. In the illustrated example, the arm section 5031 includes multiple joint sections 5033a, 5033b, and 5033c, as well as multiple links 5035a and 5035b joined by the joint section 5033b, but in FIG. 1, for the sake of simplicity, the configuration of the arm section 5031 is illustrated in a simplified manner. In actuality, the shapes, numbers, and arrangement of the joint sections 5033a to 5033c and the links 5035a and 5035b, the directions of the rotation axes of the joint sections 5033a to 5033c, and the like may be set appropriately so that the arm section 5031 has the desired degrees of freedom. For example, the arm section 5031 preferably may be configured to have six or more degrees of freedom. With this arrangement, it is possible to move the endoscope 5001 freely within the movable range of the arm section 5031, and thus it becomes possible to insert the lens tube 5003 of the endoscope 5001 into the body cavity of the patient 5071 from a desired direction.

The joint sections 5033a to 5033c are provided with actuators, and the joint sections 5033a to 5033c are configured to be rotatable about a certain rotation axis in accordance with the driving of the actuators. By controlling the driving of the actuators with the arm control apparatus 5045, the rotational angle of each of the joint sections 5033a to 5033c is controlled, and the driving of the arm section 5031 is controlled. With this arrangement, the position and the attitude of the endoscope 5001 may be controlled. At this point, the arm control apparatus 5045 is able to control the driving of the arm section 5031 with any of various known types of control methods, such as force control or position control.

For example, by having the surgeon 5067 perform appropriate operation input via an input apparatus 5047 (including a footswitch 5057), the driving of the arm section 5031 may be controlled appropriately by the arm control apparatus 5045 in accordance with the operation input, and the position and the attitude of the endoscope 5001 may be controlled. By such control, after moving the endoscope 5001 on the front end of the arm section 5031 from an arbitrary position to an arbitrary position, the endoscope 5001 can be supported securely at the position after the move. Note that the arm section 5031 may be operated by what is called a master-slave method. In this case, the arm section 5031 may be operated remotely by a user via the input apparatus 5047 installed in a location distanced from the operating room.

Further, in the case in which force control is applied, the arm control apparatus 5045 receives the external force by the user, and may execute what is called power assist control, in which the actuators of each of the joint sections 5033*a* to 5033*c* are driven so that the arm section 5031 moves smoothly following the external force. With this arrangement, when the user moves the arm section 5031 while touching the arm section 5031 directly, the arm section 5031 can be moved with comparatively light force. Consequently, it becomes possible to move the endoscope 5001 more intuitively with a simpler operation, and convenience for the user can be improved.

Herein, in endoscopic surgery, typically the endoscope 5001 has been supported by a doctor called a scopist. In contrast, by using the support arm apparatus 5027, it becomes possible to keep the position of the endoscope 5001 fixed more reliably without manual work, and thus image of the operating site can be obtained consistently, making it possible to perform surgery smoothly.

Note that the arm control apparatus 5045 does not necessarily have to be provided on the cart 5037. Also, the arm control apparatus 5045 does not necessarily have to be a single device. For example, the arm control apparatus 5045 may also be proved respectively in each of the joint sections 5033*a* to 5033*c* of the arm section 5031 of the support arm apparatus 5027, and the multiple arm control apparatus 5045 may cooperate with each other to realize driving control of the arm section 5031.

<1-5. Light Source Apparatus>

The light source apparatus 5043 supplies irradiating light to the endoscope 5001 when the operating site is imaged. For example, the light source apparatus 5043 is configured as a white light source which includes an LED, a laser light source, or a combination thereof. At this time, when the white light source includes a combination of RGB laser light sources, since an output intensity and an output timing of each color (each wavelength) can be controlled with high precision, it is possible to adjust the white balance of the captured image in the light source apparatus 5043. In addition, in this case, by irradiating an observation target with laser light from each of the RGB laser light sources in a time-division manner and controlling driving of the image sensor of the camera head 5005 in synchronization with irradiation timing, it is also possible to capture an image corresponding to each of RGB in a time-division manner. According to this method, a color image can be obtained even when a color filter is not provided in the image sensor.

Driving of the light source apparatus 5043 may also be controlled so that an intensity of output light is changed at predetermined intervals. By controlling driving of the image sensor of the camera head 5005 in synchronization with timing at which the intensity of light is changed to acquire images in a time-division manner and compositing the images, a high dynamic range image without so-called "black fullness" or "overexposure" can be generated.

The light source apparatus 5043 may also be configured to supply light in a predetermined wavelength range corresponding to special light observation. In the special light observation, for example, so-called "narrow band imaging" in which, by using the wavelength dependence of light absorption in a body tissue and irradiating narrow-band light in comparison to the irradiating light (that is, white light) at the time of ordinary observation, a predetermined tissue such as a blood vessel of mucous membrane surface layer is imaged with high contrast is performed. Alternatively, in the special light observation, fluorescence observation in which an image is obtained by fluorescence generated due to irradiation of excitation light may be performed. In the fluorescence observation, a body tissue may be irradiated with excitation light to observe fluorescence from the body tissue (autofluorescence observation), or a reagent such as indocyanine green (ICG) is locally administered to the body tissue and the body tissue is irradiated with excitation light corresponding to a fluorescence wavelength of the reagent to obtain a fluorescence image. The light source apparatus 5043 may be configured to supply narrow-band light and/or excitation light which correspond to such special light observation.

<1-6. Camera Head and CCU>

Figure 2:
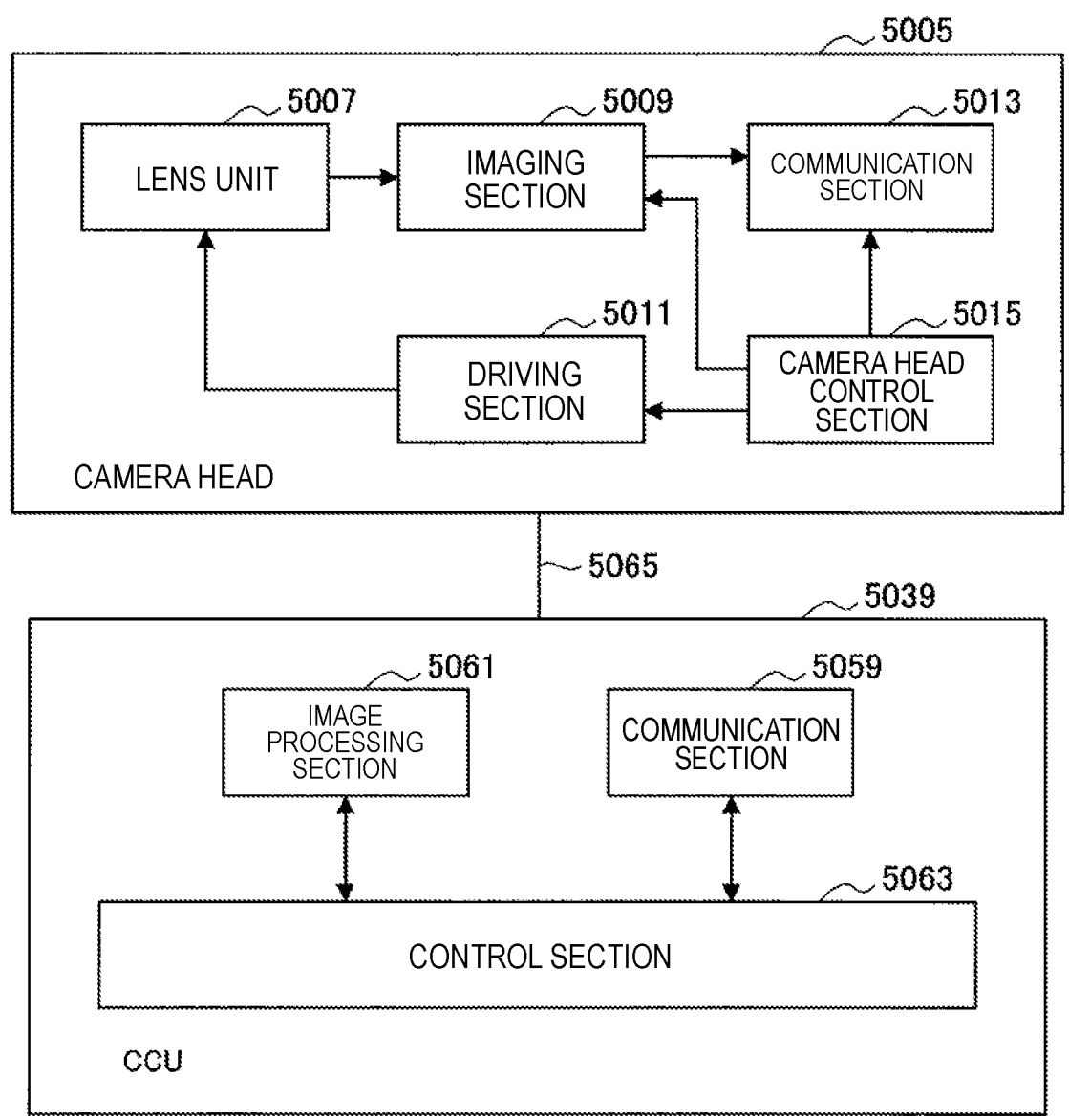
FIG. 2 is a block diagram illustrating an example of a functional configuration of the camera head and the CCU illustrated in FIG. 1.

The functions of the camera head 5005 and the CCU 5039 of the endoscope 5001 will be described in further detail with reference to FIG. 2. FIG. 2 is a block diagram illustrating an example of a functional configuration of the camera head 5005 and the CCU 5039 illustrated in FIG. 1.

Referring to FIG. 2, functionally, the camera head 5005 includes a lens unit 5007, an imaging section 5009, a driving section 5011, a communication section 5013, and a camera head control section 5015. Also, functionally, the CCU 5039 includes a communication section 5059, an image processing section 5061, and a control section 5063. The camera head 5005 and the CCU 5039 are bidirectionally communicably connected by a transmission cable 5065.

First, a functional configuration of the camera head 5005 will be described. The lens unit 5007 is an optical system provided in the part that connects to the lens tube 5003. Observation light taken in from the front end of the lens tube 5003 is guided up to the camera head 5005, and is incident on the lens unit 5007. The lens unit 5007 includes a combination of multiple lenses, including a zoom lens and a focus lens. The optical characteristics of the lens unit 5007 are adjusted to condense observation light onto the photosensitive face of an image sensor in the imaging section 5009. Also, the zoom lens and the focus lens are configured to be able to move position on the optical axis to adjust the magnification and the focus of the captured image.

The imaging section 5009 includes an image sensor, and is disposed downstream from the lens unit 5007. Observation light passing through the lens unit 5007 is condensed onto the photosensitive face of the image sensor, and by photoelectric conversion, an image signal corresponding to the observed image is generated. The image signal generated by the imaging section 5009 is provided to the communication section 5013.

For the image sensor included in the imaging section 5009, a complementary metal-oxide semiconductor (CMOS) type image sensor having a Bayer array to enable color imaging is used, for example. Note that a sensor capable of capturing high-resolution images of 4K or greater may be used as the image sensor, for example. By obtaining a high-resolution image of the operating site, the surgeon 5067 becomes able to grasp the state of the operating site in greater detail, and proceed with surgery more smoothly.

Also, the image sensor included in the imaging section 5009 is configured to include a pair of image sensors for acquiring an image signal for each of the right eye and the left eye corresponding to 3D display. By presenting a 3D display, the surgeon 5067 becomes able to grasp the depth of biological tissue at the operating site more accurately. Note that if the imaging section 5009 has a multi-chip configuration, the lens unit 5007 likewise is provided with multiple subsystems corresponding to each of the image sensors.

Also, the imaging section 5009 does not necessarily have to be provided in the camera head 5005. For example, the imaging section 5009 may also be provided inside the lens tube 5003, directly behind the objective lens.

The driving section 5011 includes actuators, and under control from the camera head control section 5015, moves the zoom lens and the focus lens of the lens unit 5007 by a predetermined distance along the optical axis. With this arrangement, the magnification and the focus of the image captured by the imaging section 5009 may be adjusted appropriately.

The communication section 5013 includes a communication apparatus for transmitting and receiving various information to and from the CCU 5039. The communication section 5013 transmits an image signal obtained from the imaging section 5009 as RAW data to the CCU 5039 through the transmission cable 5065. At this point, to display the captured image of the operating site with low latency, the image signal preferably is transmitted by optical communication. This is because during surgery, the surgeon 5067 performs surgery while observing the state of the affected area via the captured image, and thus for safer and more reliable surgery, there is demand for the moving image of the operating site to be displayed as close to real-time as possible. In the case in which optical communication is conducted, the communication section 5013 is provided with a photoelectric conversion module that converts an electrical signal into an optical signal. The image signal is converted into an optical signal by the photoelectric conversion module, and then transmitted to the CCU 5039 through the transmission cable 5065.

Also, the communication section 5013 receives, from the CCU 5039, a control signal for controlling the driving of the camera head 5005. The control signal includes information related to imaging parameters, such as information specifying the frame rate of the captured image, information specifying the exposure value during imaging, and/or information specifying the magnification and focus of the captured image, for example. The communication section 5013 provides the received control signal to the camera head control section 5015. Note that the control signal from the CCU 5039 may also be transmitted by optical communication. In this case, the communication section 5013 is provided with a photoelectric conversion module that converts an optical signal into an electrical signal, whereby the control signal is converted into an electrical signal by the photoelectric conversion module, and then provided to the camera head control section 5015.

Note that the above imaging parameters such as the frame rate, the exposure value, the magnification, and the focus are set automatically by the control section 5063 of the CCU 5039 on the basis of the acquired image signal. In other words, what are called an auto exposure (AE) function, an auto focus (AF) function, and an auto white balance (AWB) function are provided in the endoscope 5001.

The camera head control section 5015 controls the driving of the camera head 5005 on the basis of a control signal from the CCU 5039 received via the communication section 5013. For example, the camera head control section 5015 controls the driving of the image sensor of the imaging section 5009, on the basis of information specifying the frame rate of the captured image and/or information specifying the exposure during imaging. As another example, the camera head control section 5015 appropriately moves the zoom lens and the focus lens of the lens unit 5007 via the driving section 5011, on the basis of information specifying the magnification and the focus of the captured image. Additionally, the camera head control section 5015 may also be provided with a function of storing information for identifying the lens tube 5003 and the camera head 5005.

Note that by disposing parts of the configuration, such as the lens unit 5007 and the imaging section 5009, inside a highly airtight and waterproof sealed structure, the camera head 5005 can be made to withstand an autoclaving sterilization process.

Next, a functional configuration of the CCU 5039 will be described. The communication section 5059 includes a communication apparatus for transmitting and receiving various information to and from the camera head 5005. The communication section 5059 receives an image signal transmitted from the camera head 5005 through the transmission cable 5065. At this point, as described earlier, the image signal preferably may be transmitted by optical communication. In this case, to support optical communication, the communication section 5059 is provided with a photoelectric conversion module that converts an optical signal into an electrical signal. The communication section 5059 provides the image signal converted into an electrical signal to the image processing section 5061.

Also, the communication section 5059 transmits, to the camera head 5005, a control signal for controlling the driving of the camera head 5005. The control signal may also be transmitted by optical communication.

The image processing section 5061 performs various types of image processing on the image signal, which is RAW data transmitted from the camera head 5005. The image processing includes any of various known types of signal processing, such as a development process, an image quality-improving process (such as a band enhancement process, a super-resolution process, a noise reduction (NR) process, and/or a shake correction process), and/or an enlargement process (digital zoom process), for example. Also, the image processing section 5061 executes a wave detection process on the image signal to execute AE, AF, and AWB.

The image processing section 5061 includes a processor such as a CPU or a GPU, and by having the processor operate in accordance with a predetermined program, the image processing and wave detection process described above may be executed. Note that in the case in which the image processing section 5061 includes multiple GPUs, the image processing section 5061 appropriately divides up information related to the image signal, and executes image processing in parallel with the multiple GPUs.

The control section 5063 executes various types of control related to the imaging of the operating site by the endoscope 5001 and the display of the captured image therefrom. For example, the control section 5063 generates a control signal for controlling the driving of the camera head 5005. At this point, in a case in which imaging parameters are input by the user, the control section 5063 generates a control signal on the basis of the input by the user. Alternatively, in a case in which the endoscope 5001 is provided with an AE function, an AF function, and an AWB function, the control section 5063 appropriately computes an optimal exposure value, focal length, and white balance in accordance with the results of the wave detection process by the image processing section 5061, and generates a control signal.

In addition, the control section 5063 causes the display apparatus 5041 to display an image of the operating site on the basis of the image signal subjected to image processing by the image processing section 5061. At this point, the control section 5063 uses any of various types of image recognition technology to recognize various objects in the operating site image. For example, by detecting the edge shapes, colors, and the like of objects included in the operating site image, the control section 5063 is able to recognize surgical instruments such as forceps, specific biological sites, hemorrhaging, mist during usage of the energy treatment tool 5021, and the like. When causing the display apparatus 5041 to display an image of the operating site, the control section 5063 uses the recognition results to overlay various surgical assistance information onto the image of the operating site. By overlaying surgical assistance information for display to be presented to the surgeon 5067, it becomes possible to proceed with surgery more safely and reliably.

The transmission cable 5065 that connects the camera head 5005 and the CCU 5039 is an electrical signal cable supporting the communication of electrical signals, optical fiber supporting optical communication, or a composite cable of the above.

Herein, in the illustrated example, communication is executed in a wired manner using the transmission cable 5065, but communication between the camera head 5005 and the CCU 5039 may also be executed wirelessly. In the case in which the communication between the two is executed wirelessly, it is no longer necessary to lay down the transmission cable 5065 inside the operating room, and thus a situation in which the movement of medical staff inside the operating room is impeded by the transmission cable 5065 may be resolved.

2. First Embodiment

Next, a configuration example of a jig holding apparatus according to a first embodiment of the present disclosure will be described in detail. The jig holding apparatus which will be described below is an example configured as a support arm apparatus for holding an endoscope, and a medical observation apparatus is configured by the endoscope being held by the support arm apparatus.

<2-1. Basic Configuration of Holding Mechanism>

Figure 3:
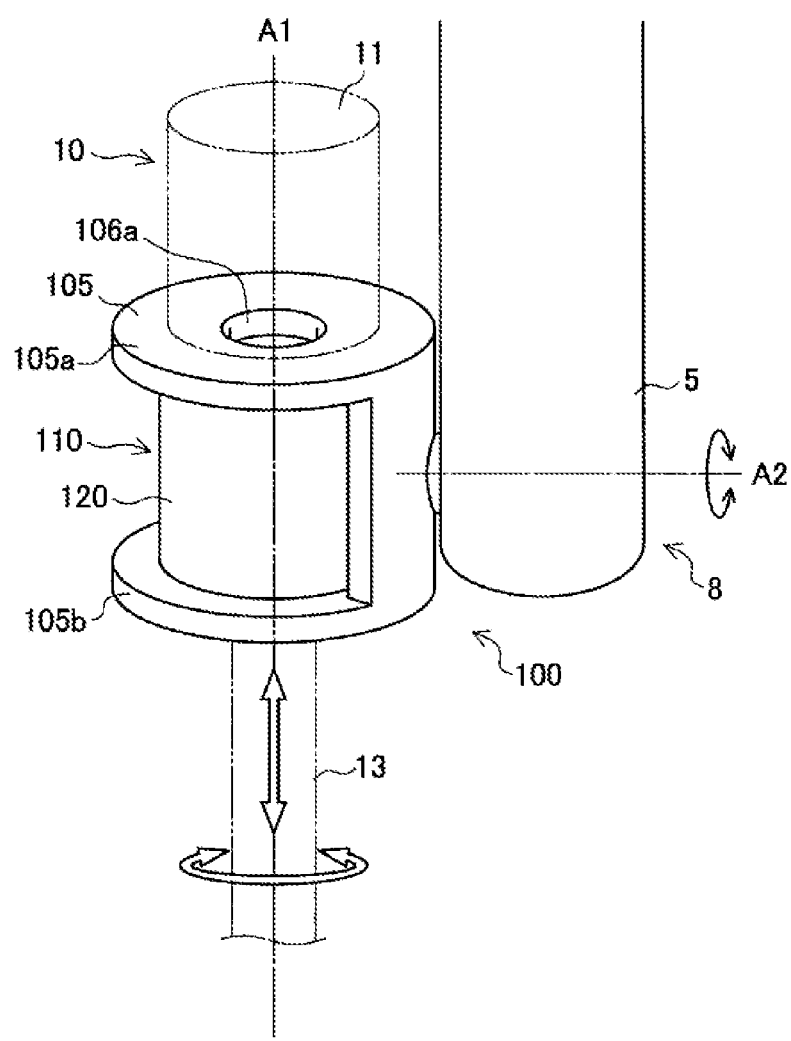
FIG. 3 is a perspective diagram illustrating a holding mechanism of a jig holding apparatus according to a first embodiment of the present disclosure.

FIG. 3 is a perspective diagram illustrating a front end section of a support arm apparatus at which a holding mechanism 100 which holds an endoscope 10 is provided. In the example illustrated in FIG. 3, the holding mechanism 100 is connected to an end section of a link 5 through a joint section 8. The holding mechanism 100 is connected to be axially rotatable about a rotation axis A2 which is perpendicular to a longitudinal direction of the link 5. An actuator (not illustrated) is provided at such a joint section 8, and the holding mechanism 100 rotates about the rotation axis A2 in response to a control command from the arm control apparatus 5045.

The holding mechanism 100 detachably holds the endoscope 10. An axis A1 of the endoscope 10 held by the holding mechanism 100 is perpendicular to the rotation axis A2. That is, the axis A1 of the endoscope 10 is disposed on a plane parallel with the longitudinal direction of the link 5, and the endoscope 10 is held by the holding mechanism 100 to be rotatable on the plane. However, a direction of the axis A1 of the endoscope 10 held by the holding mechanism 100 is not limited to such an example.

The holding mechanism 100 includes a holding case 105 and a driving section 110. The driving section 110 is fixed to the holding case 105. The holding case 105 has end face sections 105*a* and 105*b* formed at both end sections in a direction at least along the axis A1 of the endoscope 10, and openings 106*a* and 106*b* are respectively provided at the end face sections 105*a* and 105*b* at a central section including the axis A1 (the opening 106*b* is not illustrated in FIG. 3). However, the form of the holding case 105 is not limited to such an example.

The driving section 110 is formed in a hollow shape having an opening along the axis A1 at the central section including the axis A1. All of the opening of the driving section 110 and the openings 106*a* and 106*b* of the holding case 105 are provided about the axis A1. A lens tube 13 of the endoscope 10 is inserted into the openings 106*a* and 106*b* of the holding case 105 and the opening of the driving section 110. The endoscope 10 held by the holding mechanism 100 illustrated in FIG. 3 is a hard mirror, and the lens tube 13 of the endoscope 10 is inserted into the holding mechanism 100 from a front end side.

The driving section 110 of the holding mechanism 100 includes a rotation driving section configured to cause the endoscope 10 to rotate about the axis A1 and a linear motion driving section configured to cause the endoscope 10 to linearly move in the direction of the axis A1. The rotation driving section and the linear motion driving section are driven by a control command from the arm control apparatus 5045 so that the endoscope 10 is rotatable about the axis A1 and is linearly movable in the direction of the axis A1. Therefore, a capturing direction of the endoscope 10 is controlled by the driving section 110 with two degrees of freedom disposed to surround the lens tube 13.

Figure 4:
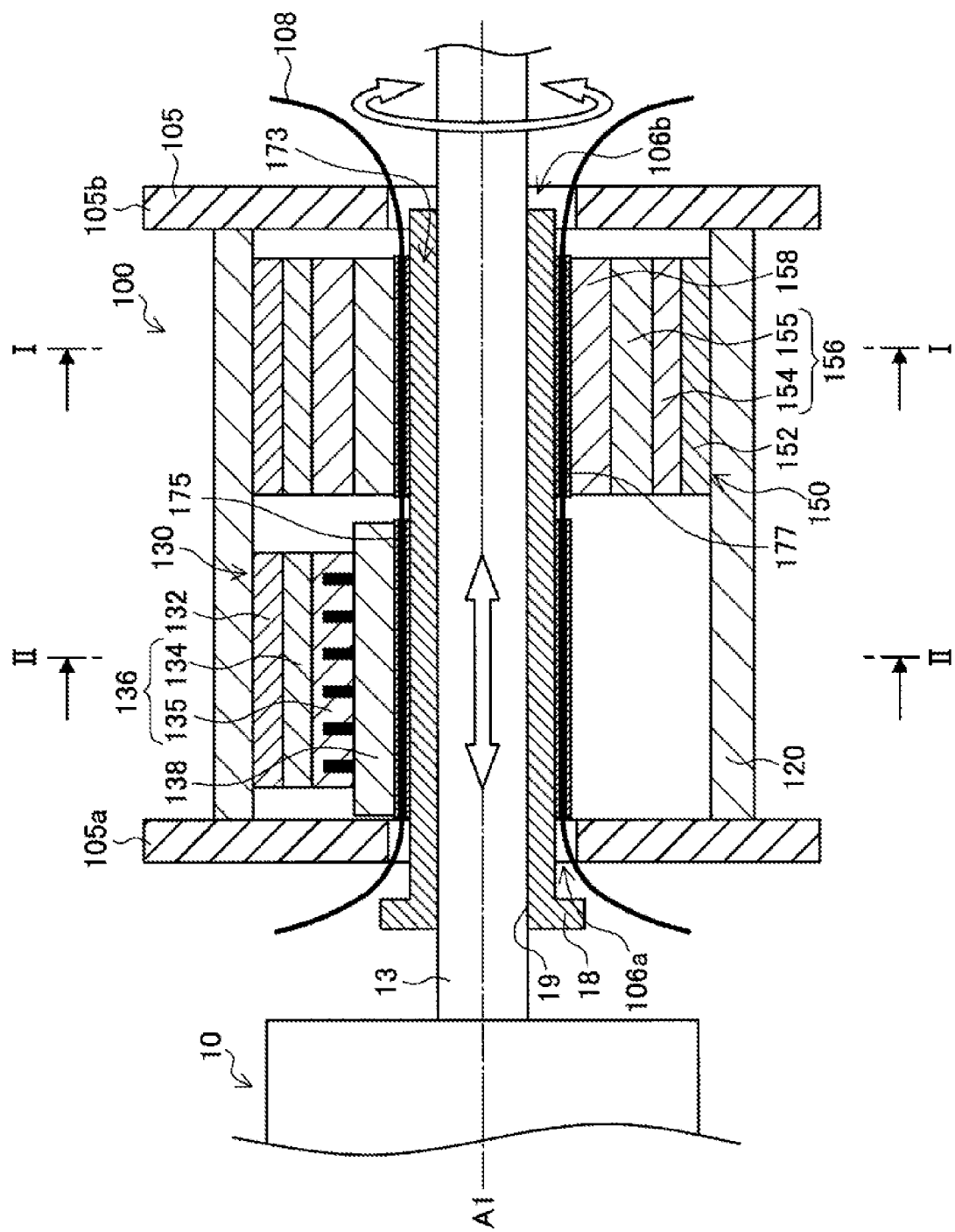
FIG. 4 is a cross-sectional diagram illustrating a configuration example of the holding mechanism of the jig holding apparatus according to the embodiment.
Figure 5:
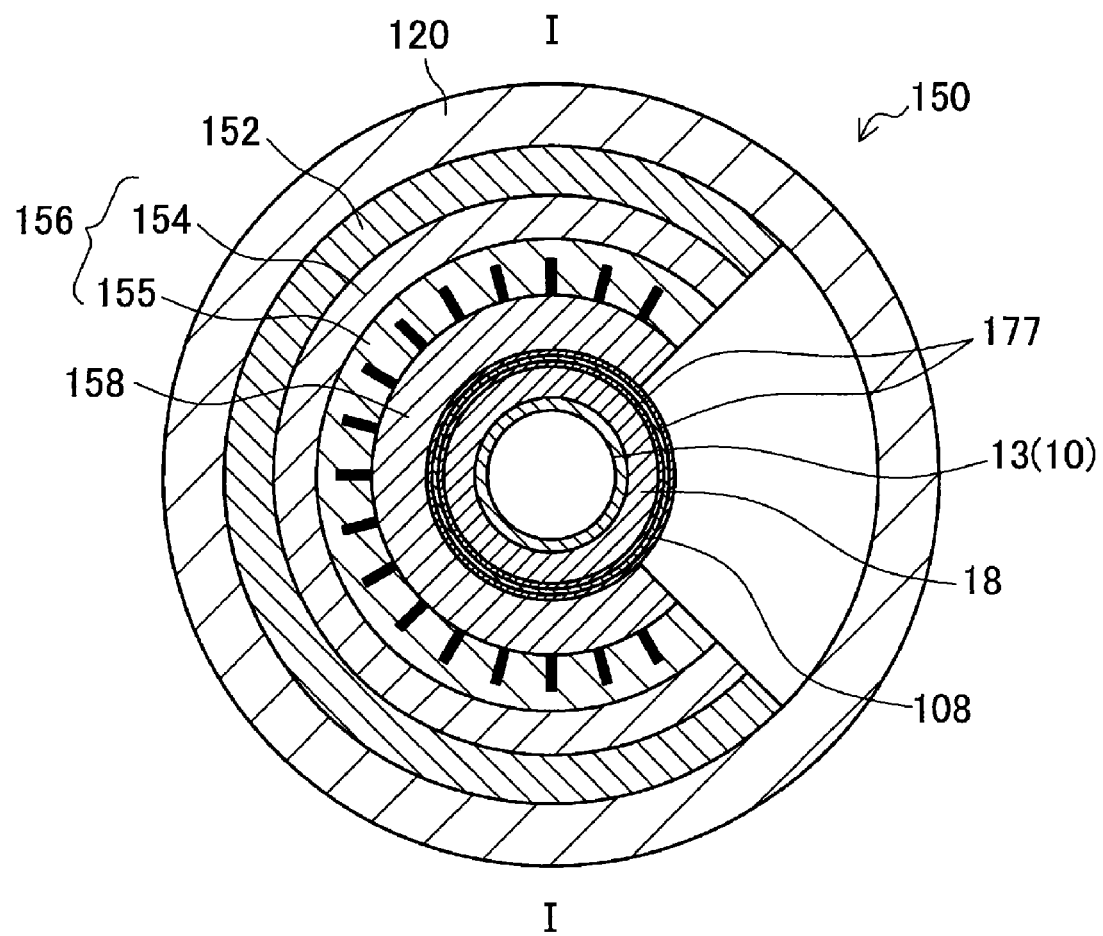
FIG. 5 is a schematic diagram illustrating a cross-section of the holding mechanism taken along line I-I of FIG. 4.
Figure 6:
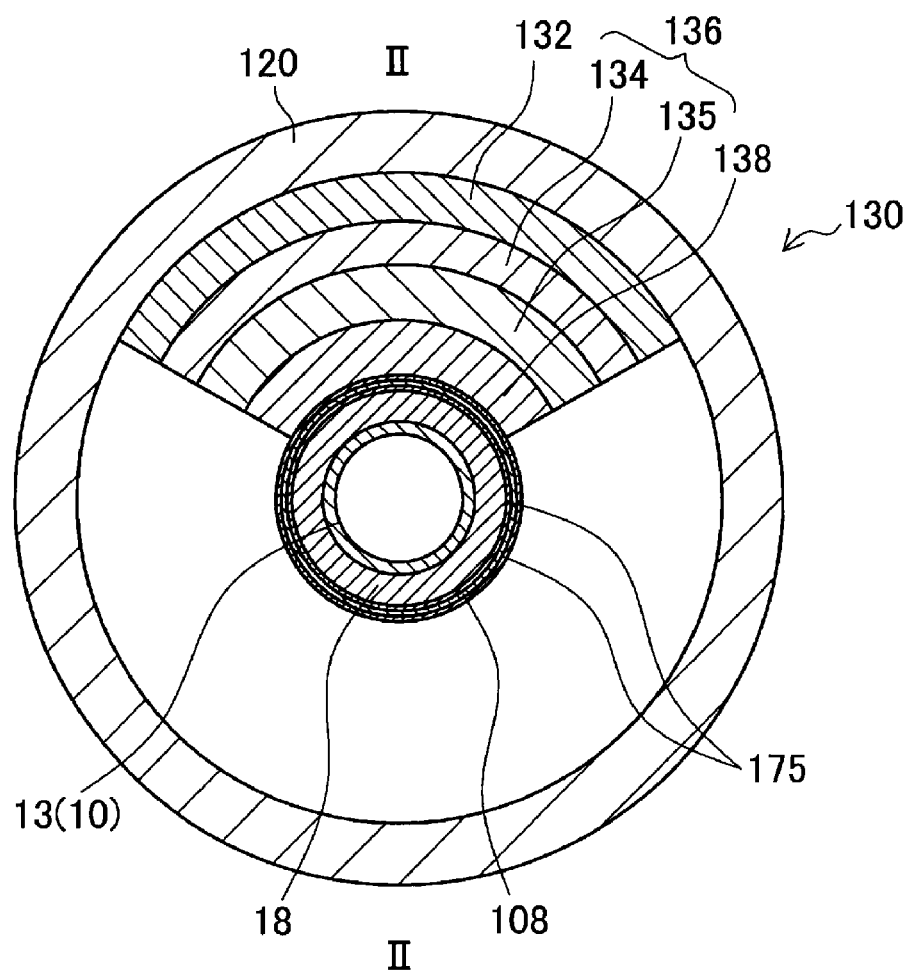
FIG. 6 is a schematic diagram illustrating a cross-section of the holding mechanism taken along line II-II of FIG. 4.

FIG. 4 is a schematic diagram illustrating a cross-section including the axis A1 in the holding mechanism 100 holding the endoscope 10. FIG. 6 is a schematic diagram illustrating a cross-section of the holding mechanism 100 taken along line I-I of FIG. 4 in the holding mechanism 100 holding the endoscope 10, and FIG. 5 is a schematic diagram illustrating a cross-section of the holding mechanism 100 taken along line II-II of FIG. 4 in the holding mechanism 100 holding the endoscope 10.

The driving section 110 of the holding mechanism 100 includes, inside a case 120, a linear motion driving section 130 and a rotation driving section 150. The case 120 has a cylindrical shape and is fixed to the holding case 105. Inside the case 120, the linear motion driving section 130 and the rotation driving section 150 are disposed in series along the axis A1, which is oriented in a direction of linear motion by the linear motion driving section 130. The linear motion driving section 130 is disposed at a base end side of the endoscope 10, and the rotation driving section 150 is disposed at a front end side of the endoscope 10. The positions at which the linear motion driving section 130 and the rotation driving section 150 are disposed may be switched. In the holding mechanism 100 according to the present embodiment, each of the linear motion driving section 130 and the rotation driving section 150 includes an ultrasonic motor.

The driving section 110 has a holding section 173 configured to hold the lens tube 13 of the endoscope 10 from a periphery thereof at the central section including the axis A1. The linear motion driving section 130 and the rotation driving section 150 are disposed around the held lens tube 13 of the endoscope 10. In the jig holding apparatus according to the present embodiment, the rotation driving section 150 is mostly in charge of a function of holding the lens tube 13 of the endoscope 10. For this reason, a hollow portion inside the rotation driving section 150 is configured as the holding section 173.

<2-2. Rotation Driving Section>

The rotation driving section 150 includes an ultrasonic motor. The rotation driving section 150 includes a mover 158, a stator 156 having a piezoelectric body 154 and a metallic body 155, and a preload mechanism 152. The mover 158, the stator 156, and the preload mechanism 152 are provided in a substantially concentric shape about the axis A1, and the mover 158, the stator 156, and the preload mechanism 152 are disposed from the central side toward the outside in that order.

As illustrated in FIG. 5, the mover 158, the stator 156, and the preload mechanism 152 are provided in the range of 270° about the axis A1. The range in which each of the members is provided is not limited to 270° and may be set as an appropriate range. However, in order cause the endoscope 10 to be held at the hollow portion of the rotation driving section 150, the rotation driving section 150 may be provided within a range that exceeds at least 180° about the axis A1. Also, in order to cause the endoscope 10 to axially rotate within a range of plus or minus 180° by the rotation driving section 150, the rotation driving section 150 may be provided within a range that exceeds at least 270° about the axis A1.

The lens tube 13 of the endoscope 10 is held through a drape 108 at an inner peripheral section of the mover 158 disposed at a side closest to the center from among the mover 158, the stator 156, and the preload mechanism 152 which constitute the rotation driving section 150. The inner peripheral section of the mover 158 serves as the holding section 173 configured to hold the endoscope 10. In the present embodiment, a fixing member 18 is mounted at an outer periphery of the lens tube 13 of the endoscope 10, and through such a fixing member 18, the lens tube 13 is held by the mover 158. The drape 108 is clamped by a drape clamping body 177 including, for example, a vinyl resin or the like and is disposed between the mover 158 and the lens tube 13. The drape clamping body 177 configured to clamp the drape 108 has a tubular shape which surrounds an entire circumference of the lens tube 13. Note that such a drape clamping body 177 may also be omitted.

The preload mechanism 152 of the rotation driving section 150 causes generation of a predetermined preload for holding the lens tube 13 inserted into the inner peripheral section of the mover 158. Since the rotation driving section 150 is provided in the range of 270° about the axis A1 instead of being continuous about an entire circumference of the axis A1 (see FIG. 5), the rotation driving section 150 is slightly bent toward the inner peripheral side by the preload, and the lens tube 13 of the endoscope 10 is held. The preload generated by the preload mechanism 152 may serve as a brake force when rotation of the lens tube 13 caused by the rotation driving section 150 is caused to stop. The preload mechanism 152 is configured using, for example, a coil spring, a leaf spring, an elastic rubber, an elastic resin, or the like. Although the preload mechanism 152 is schematically illustrated as a layer in each drawing, the preload mechanism 152 may not be formed as a layer in actuality.

Figure 7:
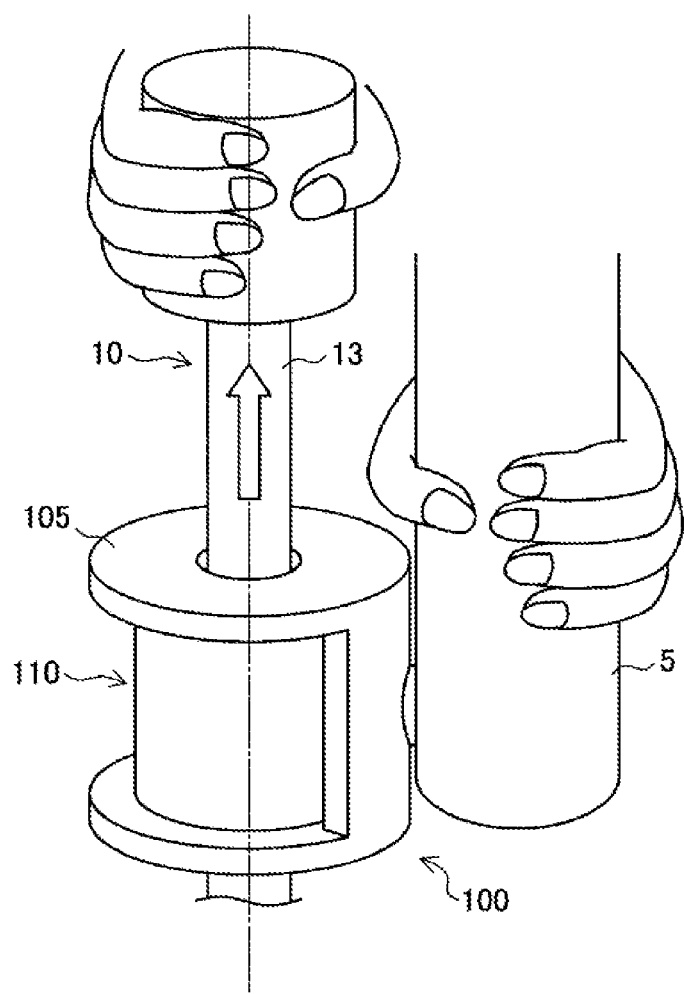
FIG. 7 is an explanatory diagram illustrating a state in which an endoscope is detached from the holding mechanism.

However, in a case in which the support arm apparatus is a medical apparatus configured to support the endoscope 10 or the like, and in a case in which a malfunction has occurred in the support arm apparatus or the like while a jig such as the endoscope 10 is inserted into a body cavity of a patient, there is a need to promptly draw out the jig from inside the body cavity. In this case, it is preferable that the endoscope 10 be promptly drawn out by a user's hand as illustrated in FIG. 7. For this reason, a force with which the endoscope 10 is held due to the preload of the preload mechanism 152 is preferably a force that is sufficient for the user to draw out the endoscope 10 by hand. On the other hand, in a case in which the holding force is small, there is a concern that a brake force when the driving control by the rotation driving section 150 or the linear motion driving section 130 is caused to stop may be insufficient. For example, in a case in which a weight of the endoscope 10 is set as 500 g and a coefficient of friction between the fixing member 18 and the holding mechanism 100 is set as 0.5, the holding force for holding the endoscope 10 may be set as a value within the range of 10 to 20N. For the user to manually draw out the endoscope 10 from the holding mechanism 100, an upper limit value of the holding force may be set as, for example, about 100N.

The mover 158 may be configured of, for example, a metal material. The mover 158 holds the lens tube 13 of the endoscope 10 at the inner peripheral section. The mover 158 abuts the stator 156 at an outer peripheral surface. The mover 158 and the stator 156 abut each other at a relatively high pressure due to the preload added by the preload mechanism 152. Therefore, the mover 158 and the endoscope 10 are held with a relatively large holding force even when energization to the rotation driving section 150 is stopped. Such a holding force may serve as a brake force in a case in which energization to the rotation driving section 150 is stopped. For this reason, a compact actuator can be realized without a brake mechanism.

The stator 156 has the piezoelectric body 154 and the metallic body 155. For example, a piezoelectric ceramic is used for the piezoelectric body 154, and the piezoelectric body 154 is disposed to be fixed on the metallic body 155 which abuts the mover 158. Although the piezoelectric body 154 is illustrated as a layer in the drawings, in actuality, a plurality of piezoelectric members divided in a circumferential direction are disposed on the metallic body 155. Each piezoelectric member is deformed due to a voltage applied thereto. Specifically, the piezoelectric members elongate in a radial direction when a voltage is applied thereto and contract in the radial direction when the voltage application is stopped.

The metallic body 155 has a comb-tooth shape having comb teeth divided in the circumferential direction. Each piezoelectric member is fixed at a position which corresponds to one of the comb teeth. Therefore, each comb tooth advances and retracts toward and from the mover 158 in accordance with elongation and contraction of the corresponding piezoelectric member. At this time, the deformation of the piezoelectric members is amplified by the metallic body 155 and propagates to the mover 158. In such a rotation driving section 150, by applying a high-frequency voltage to the piezoelectric body 154, the individual piezoelectric members sequentially elongate and contract in the circumferential direction, and a surface of the metallic body 155 is deformed in a wave shape. The apex of this wave moves in the circumferential direction as a traveling wave and causes the mover 158, which abuts the stator 156, to rotate in the direction opposite to the traveling direction of the traveling wave by a frictional force.

To suppress wear of the mover 158 due to rotation, a sliding member may be provided on at least one of the outer peripheral surface of the mover 158 and the inner peripheral surface of the stator 156 which are in contact with each other.

A length of the rotation driving section 150 in the direction along the axis A1 may be set to be larger than at least a size of a linear motion range by the linear motion driving section 130. In this way, the endoscope 10 can be caused to rotate by the rotation driving section 150 regardless of an axial position of the endoscope 10. For the same reason, a length of the fixing member 18 mounted at the endoscope 10 is set so that at least a portion of the fixing member 18 is disposed at an inner peripheral section of the rotation driving section 150 even in a case in which the position of the endoscope 10 is changed by the linear motion driving section 130.

<2-3. Linear Motion Driving Section>

The linear motion driving section 130 includes an ultrasonic motor. The linear motion driving section 130 includes a mover 138, a stator 136 having a piezoelectric body 134 and a metallic body 135, and a preload mechanism 132. The mover 138, the stator 136, and the preload mechanism 132 are provided in a substantially concentric shape about the axis A1, and the mover 138, the stator 136, and the preload mechanism 132 are disposed from the central side toward the outside in that order. As illustrated in FIG. 6, the mover 138, the stator 136, and the preload mechanism 132 are provided in the range of 120° about the axis A1. However, the range in which each of the members is provided is not limited to 120° and may be set as an appropriate range.

The lens tube 13 of the endoscope 10 is held through the drape 108 at an inner peripheral section of the mover 138 disposed at a side closest to the center from among the mover 138, the stator 136, and the preload mechanism 132 which constitute the linear motion driving section 130. In the present embodiment, the fixing member 18 is mounted at the outer periphery of the lens tube 13 of the endoscope 10, and through such a fixing member 18, the lens tube 13 is held by the mover 138. The drape 108 is clamped by a drape clamping body 175 including, for example, a vinyl resin or the like and is disposed between the mover 138 and the lens tube 13. The drape clamping body 175 configured to clamp the drape 108 has a tubular shape which surrounds an entire circumference of the lens tube 13. Such a drape clamping body 175 may also be omitted.

The preload mechanism 132 of the linear motion driving section 130 causes generation of a predetermined preload for pressing an inner peripheral section of the mover 138 against the lens tube 13. Since the linear motion driving section 130 is provided in the range of 120° about the axis A1 instead of being continuous about the entire circumference of the axis A1, the linear motion driving section 130 is slightly bent toward the inner peripheral side by the preload, and the mover 138 is pressed against an outer peripheral surface of the lens tube 13 of the endoscope 10 with a predetermined pressing force. The preload generated by the preload mechanism 132 may serve as a brake force when linear motion of the lens tube 13 caused by the linear motion driving section 130 is caused to stop. Like the preload mechanism 152 of the rotation driving section 150, the preload mechanism 132 is configured using, for example, a coil spring, a leaf spring, an elastic rubber, an elastic resin, or the like. Although the preload mechanism 132 is schematically illustrated as a layer in each drawing, the preload mechanism 132 may not be formed as a layer in actuality.

The mover 138 may be configured of, for example, a metal material. The mover 138 holds the lens tube 13 of the endoscope 10 at the inner peripheral section. The mover 138 abuts the stator 136 at an outer peripheral surface. The mover 138 and the stator 136 abut each other at a relatively high pressure. Therefore, the mover 138 and the endoscope 10 are held with a relatively large pressing force even when energization to the linear motion driving section 130 is stopped. Such a pressing force may serve as a brake force in a case in which energization to the linear motion driving section 130 is stopped. For this reason, a compact actuator can be realized without a brake mechanism.

The stator 136 has the piezoelectric body 134 and the metallic body 135. For example, a piezoelectric ceramic is used for the piezoelectric body 134, and the piezoelectric body 134 is disposed to be fixed on the metallic body 135 which abuts the mover 138. Although the piezoelectric body 134 is illustrated as a layer in the drawings, in actuality, a plurality of piezoelectric members divided in the direction of the axis A1 are disposed on the metallic body 135. Each piezoelectric member is deformed due to a voltage applied thereto. Specifically, the piezoelectric members elongate in the radial direction when a voltage is applied thereto and contract in the radial direction when the voltage application is stopped.

The metallic body 135 has a comb-tooth shape having comb teeth divided in the direction of the axis A1. Each piezoelectric member is fixed at a position which corresponds to one of the comb teeth. Therefore, each comb tooth advances and retracts toward and from the mover 138 in accordance with elongation and contraction of the corresponding piezoelectric member. At this time, the deformation of the piezoelectric member is amplified by the metallic body 135 and propagated to the mover 138. In such a linear motion driving section 130, by applying a high-frequency voltage to the piezoelectric body 134, the individual piezoelectric members sequentially elongate and contract in the direction of the axis A1, and a surface of the metallic body 135 is deformed in a wave shape. The apex of this wave moves in the direction of the axis A1 as a traveling wave and causes the mover 138, which abuts the stator 136, to rotate in the direction opposite to the traveling direction of the traveling wave by a frictional force.

Even in the linear motion driving section 130, to suppress wear of the mover 138 due to rotation, a sliding member may be provided on at least one of the outer peripheral surface of the mover 138 and the inner peripheral surface of the stator 136 which are in contact with each other.

A length of the linear motion driving section 130 in the direction along the axis A1 may be suitably selected in accordance with a linear motion range of the endoscope 10. For example, if an attitude of the arm of the support arm apparatus is controlled in a case in which the axial position of the endoscope 10 is caused to be largely moved, and if the linear motion driving section 130 is used in a case in which the axial position of the endoscope 10 is caused to be slightly moved, the length of the linear motion driving section 130 may be 50 mm to 100 mm. In this way, fine adjustment of the position of the endoscope 10 can be performed while maintaining the attitude of the arm without increasing the size of the holding mechanism 100.

<2-4. Clean Area and Unclean Area>

The endoscope 10 is detachable in the holding mechanism 100 of the support arm apparatus according to the present embodiment. At this time, to prevent a front end of the lens tube 13 of the endoscope 10 from becoming unclean due to coming into contact with an inner structure of the holding mechanism 100 in a case in which the endoscope 10 is detached, a clean area in which the endoscope 10 inserted into a body cavity of a patient exists and an unclean area in which the inner structure of the holding mechanism 100 exists may be partitioned from each other.

Figure 8:
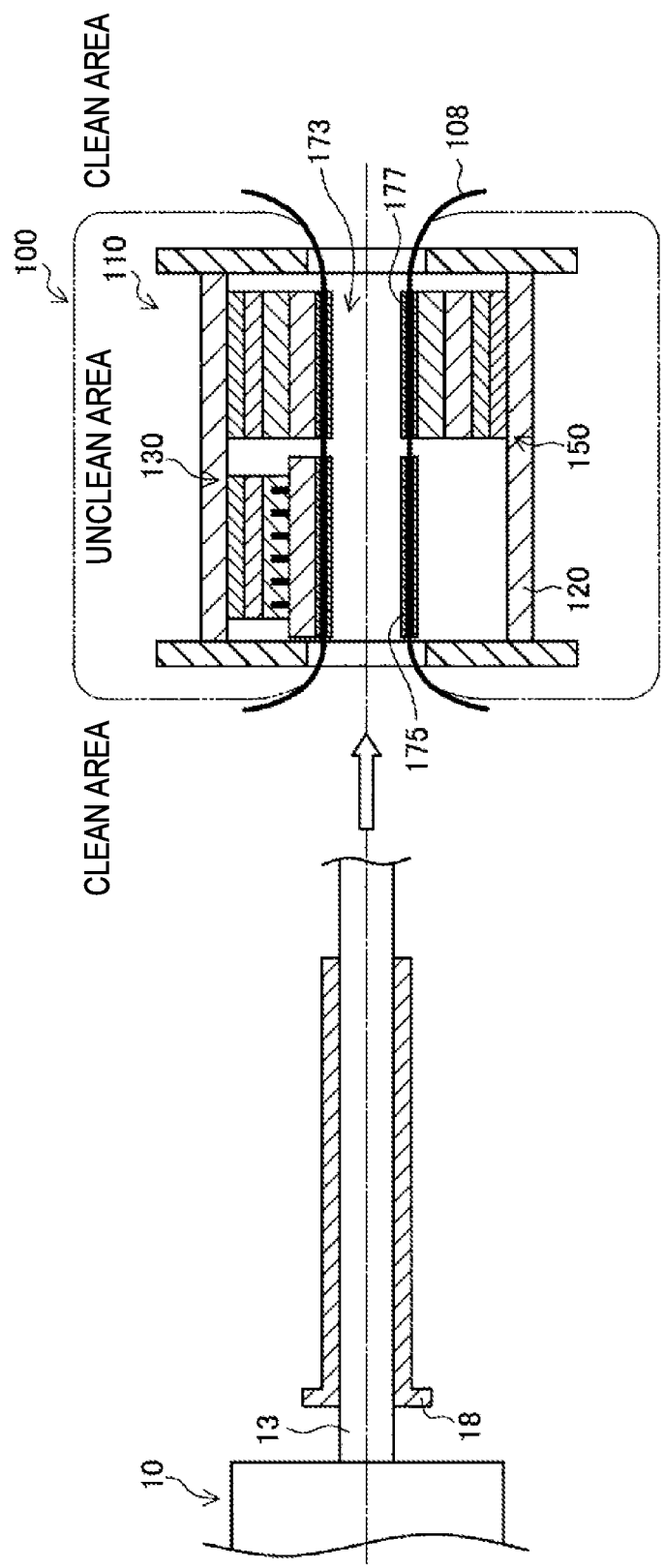
FIG. 8 is an explanatory diagram illustrating a clean area and an unclean area.

FIG. 8 is a schematic diagram illustrating a clean area and an unclean area in the vicinity of the holding mechanism 100 of the support arm apparatus. In the support arm apparatus according to the present embodiment, the fixing member 18 is mounted at the lens tube 13 of the endoscope 10, and the outer peripheral surface of the fixing member 18 is detachably held by the holding section 173 of the holding mechanism 100. The drape 108 clamped by the drape clamping bodies 175 and 177 is interposed between the mover 138 of the linear motion driving section 130 and the mover 158 of the rotation driving section 150, and the endoscope 10 can be partitioned from each member constituting the driving section 110 of the holding mechanism 100. Therefore, the holding mechanism 100 may be kept cleaner.

The fixing member 18 may be configured of a material easy to sterilize such as a metal (including light metal), and cleanliness can be guaranteed even in a case in which a jig such as the held endoscope 10 is replaced. In this way, since a jig, which is a target to be held by the holding mechanism 100, can be configured of a sterilizable material, cleanliness of the clean area can be easily maintained. Alternatively, the fixing member 18 may also be an inexpensive disposable part which is discarded after use. In a case in which the fixing member 18 is a disposable part, since a clean fixing member 18 can be used every time a jig such as the endoscope 10 to be caused to be held is replaced, cleanliness can be guaranteed.

<2-5. Positioning Mechanism>

In the support arm apparatus according to the present embodiment, a positioning mechanism for defining a holding position of the endoscope 10 may be provided in the holding mechanism 100. By providing the positioning mechanism, the endoscope 10 can be disposed at a predetermined position with respect to the holding mechanism 100. Therefore, adjustment of the position of the endoscope 10 can be more precisely performed by the support arm apparatus.

Figure 9:
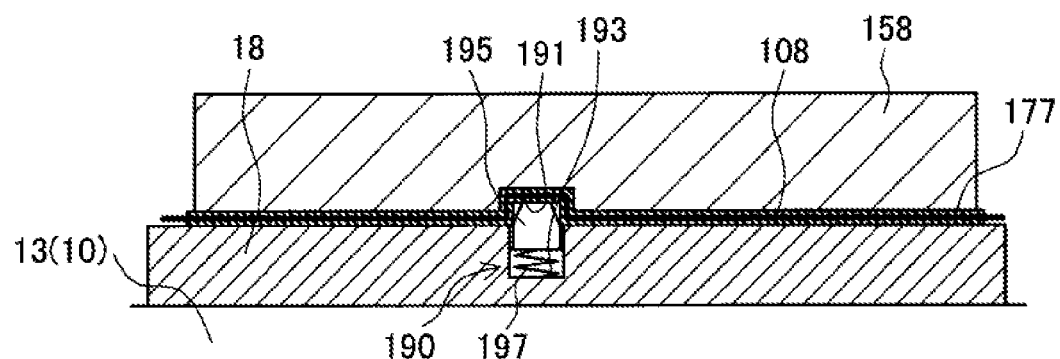
FIG. 9 is an explanatory diagram illustrating a configuration example of a positioning mechanism.
Figure 9:
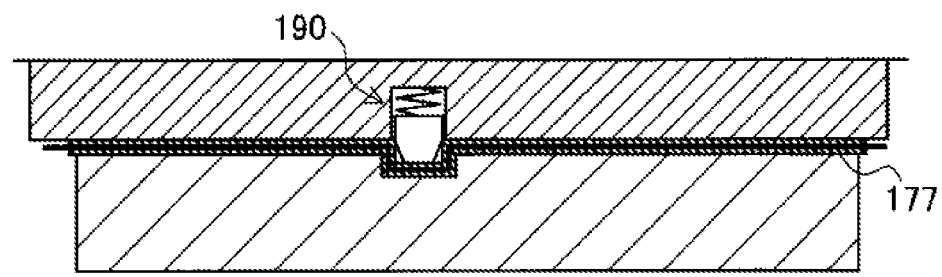

FIG. 9 is a schematic diagram illustrating a configuration example of a positioning mechanism and illustrates a positioning mechanism provided at the mover 158 of the rotation driving section 150 and the fixing member 18. Such a positioning mechanism includes a positioning pin 195 as a locking section and an engaging groove 191 as an engaging section with which the positioning pin 195 is engaged.

The positioning pin 195 is disposed inside a pin holding groove 193 provided at the outer peripheral surface of the fixing member 18 and is held by being energized in the outer peripheral direction by an energizing member 197 such as a coil spring. The engaging groove 191 is formed at the inner peripheral surface of the mover 158 so as to be open with a size that allows the positioning pin 195 to enter. In a case in which the drape 108 clamped by the drape clamping body 177 is interposed between the mover 158 and the fixing member 18, the drape clamping body 177 may have a convex section (or a concave section) which corresponds to the shape of the engaging groove 191. By such a positioning mechanism, the endoscope 10 at which the fixing member 18 is mounted is inserted into the holding section 173 of the holding mechanism 100, and by the positioning pin 195 being engaged with the engaging groove 191, the endoscope 10 can be held at a predetermined position.

Figure 10:
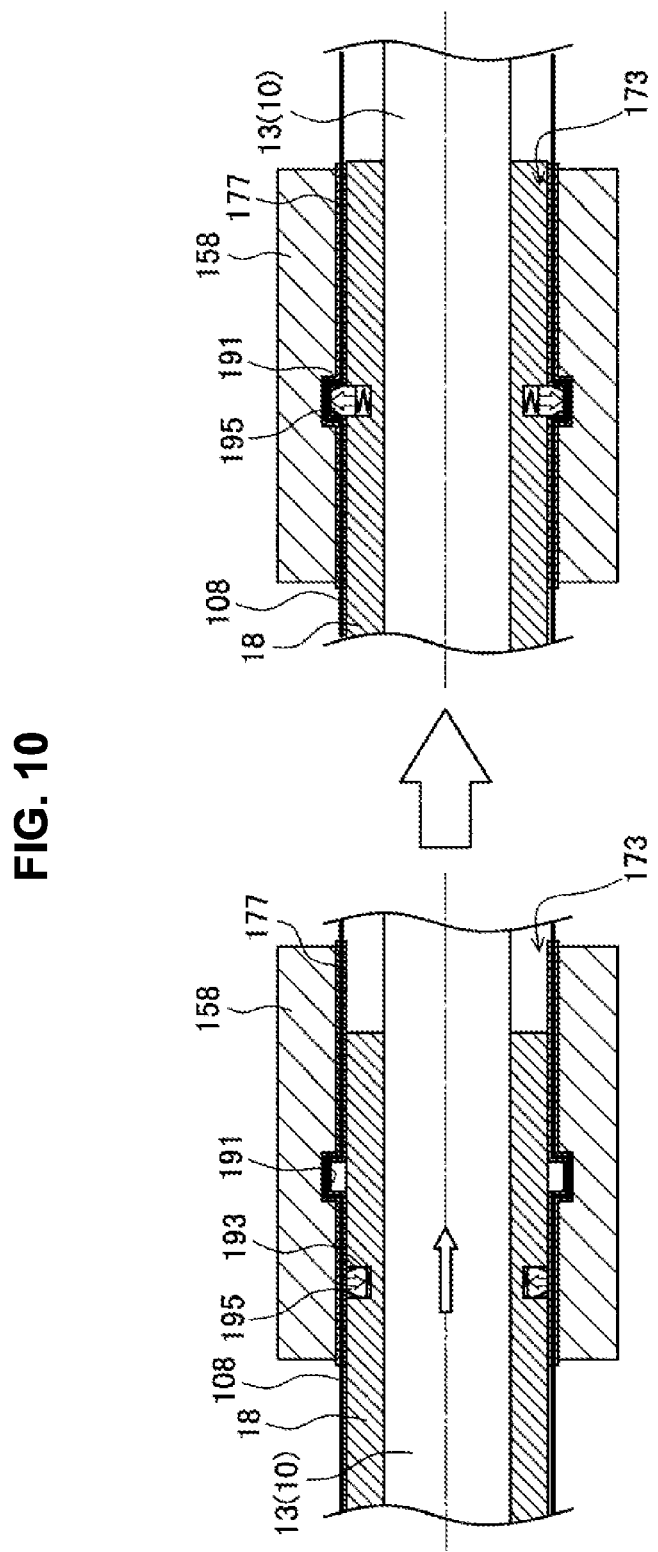
FIG. 10 is an explanatory diagram illustrating an action of the positioning mechanism at the time of attaching an endoscope.

FIG. 10 illustrates a state in which the endoscope 10 is attached to the holding mechanism 100. In a case in which the endoscope 10 is attached to the holding mechanism 100, as the lens tube 13 and the fixing member 18 are inserted into the holding section 173, the positioning pin 195 abuts an edge of the inner peripheral surface of the mover 158 and retracts in the pin holding groove 193. At this time, a surface of the positioning pin 195 on the front side in the insertion direction may be inclined toward the rear side in the insertion direction. By the positioning pin 195 having such an inclined surface, as the fixing member 18 is inserted, the positioning pin 195 is easily pushed down into the pin holding groove 193 by the edge of the inner peripheral surface of the mover 158.

Since the drape 108 is clamped by the drape clamping body 177, the drape 108 is not easily displaced or bent in the holding section 173. In this way, insertion of the lens tube 13 and the fixing member 18 is facilitated. Also, when the fixing member 18 and the lens tube 13 are moved to a position at which the positioning pin 195 faces the engaging groove 191, the positioning pin 195 enters the engaging groove 191 and is engaged therewith by an energizing force of the energizing member 197. In this way, the endoscope 10 is held at a predetermined position.

Figure 11:
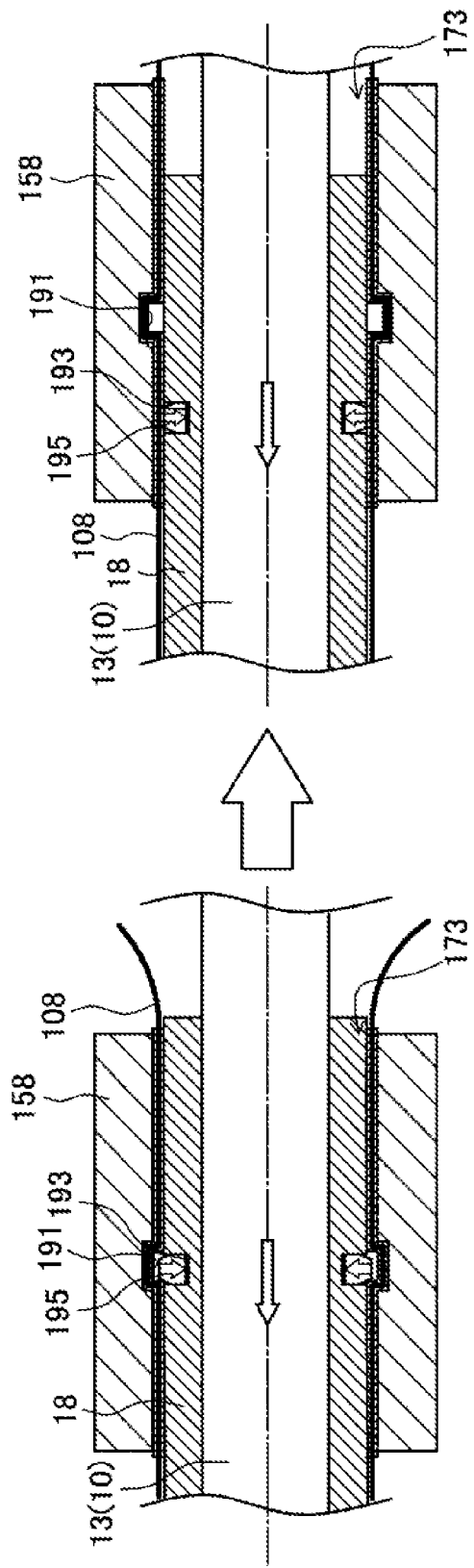
FIG. 11 is an explanatory diagram illustrating an action of the positioning mechanism at the time of detaching the endoscope.

FIG. 11 illustrates a state in which the endoscope 10 is detached from the holding mechanism 100. In a case in which the endoscope 10 is detached from the holding mechanism 100, as the lens tube 13 and the fixing member 18 are pulled from the base end side, the positioning pin 195 abuts an edge of the engaging groove 191 and retracts in the pin holding groove 193. At this time, a surface of the positioning pin 195 on the rear side in the insertion direction may be inclined toward the front side in the insertion direction. By the positioning pin 195 having such an inclined surface, as the fixing member 18 is moved, the positioning pin 195 is easily pushed down into the pin holding groove 193 by the edge of engaging groove 191.

Also, since the drape 108 is clamped by the drape clamping body 177, the drape 108 is not easily displaced in the holding section 173. In this way, detachment of the lens tube 13 and the fixing member 18 is facilitated.

Note that by the drape clamping body 177, which clamps the drape 108, having the convex section corresponding to the engaging groove 191, the positioning pin 195 can be prevented from being pulled down due to elongation of the drape 108 when an external force is applied to the drape 108 and the drape 108 is pulled while the positioning pin 195 is engaged with the engaging groove 191.

The number of positioning pins 195 and engaging grooves 191 is not particularly limited. The number of positioning pins 195 and engaging grooves 191 may be one or plural. Further, a planar shape (shape viewed from the radial direction) of the positioning pin 195 and the engaging groove 191 is not particularly limited. The planar shape of the positioning pin 195 and the engaging groove 191 may be circular, rectangular, elliptical, or any other arbitrary shape.

Note that in a case in which the lens tube 13 of the endoscope 10 is caused to be held by the holding section 173 without using the fixing member 18, the positioning pin 195 may be provided at the outer peripheral surface of the lens tube 13. Further, in a case in which the drape 108 and the drape clamping bodies 175 and 177 are not used, the positioning pin 195 may be provided at a side of the mover 158, and the engaging groove 191 may be provided at a side of the fixing member 18 or the lens tube 13.

<2-6. Expansion of Workspace>

Figure 12:
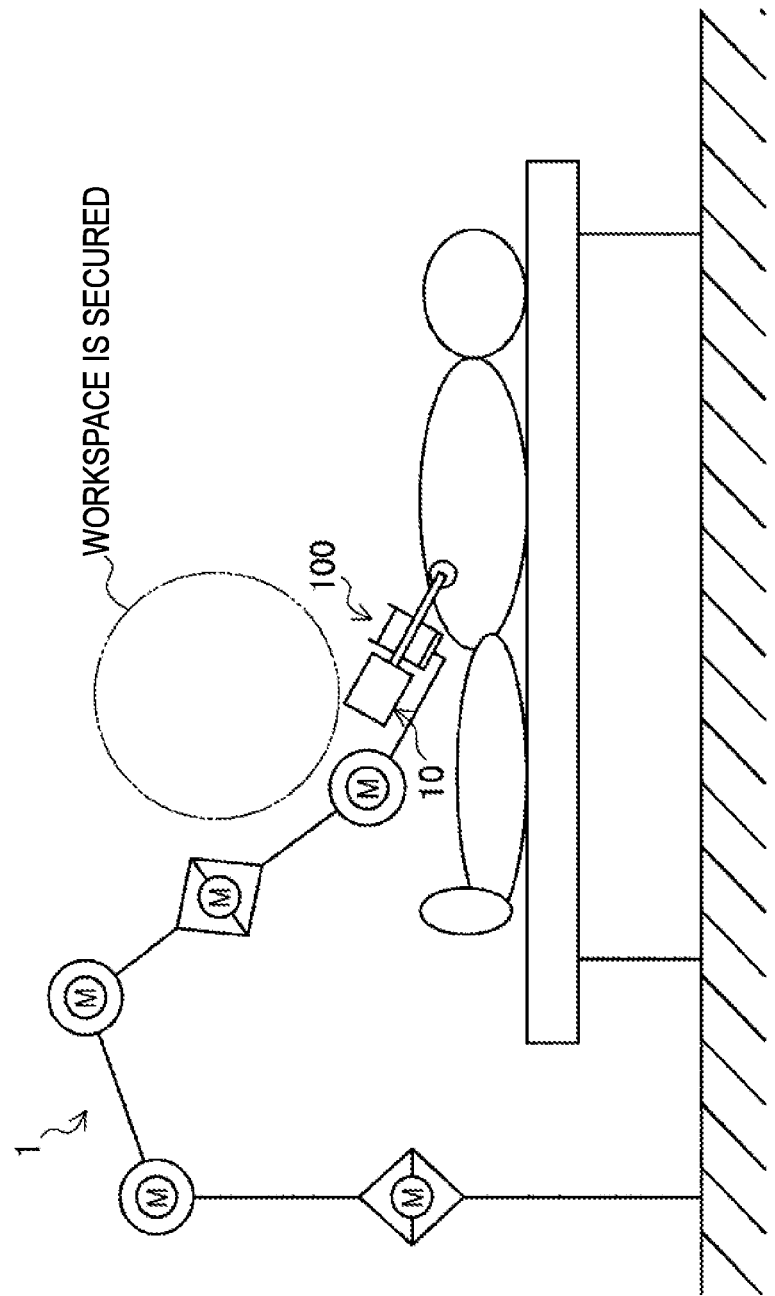
FIG. 12 is an explanatory diagram illustrating a use state of the jig holding apparatus according to the embodiment.

FIG. 12 is an explanatory diagram illustrating an expansion of a workspace in a case in which a jig holding apparatus 1 according to the present embodiment is used as a support arm apparatus of an endoscopic observation apparatus. As described above, the jig holding apparatus 1 according to the present embodiment includes the linear motion driving section 130 and the rotation driving section 150, which include an ultrasonic motor, disposed in the holding mechanism 100, and the endoscope 10 is held in the hollow portion of the rotation driving section 150 configured in a hollow shape. In this way, the driving section 110 is disposed to surround the lens tube 13 of the endoscope 10, and the configuration of the front end section of the support arm apparatus is simplified. In this way, a workspace in the vicinity of the front end section of the jig holding apparatus 1 is secured.

Figure 13:
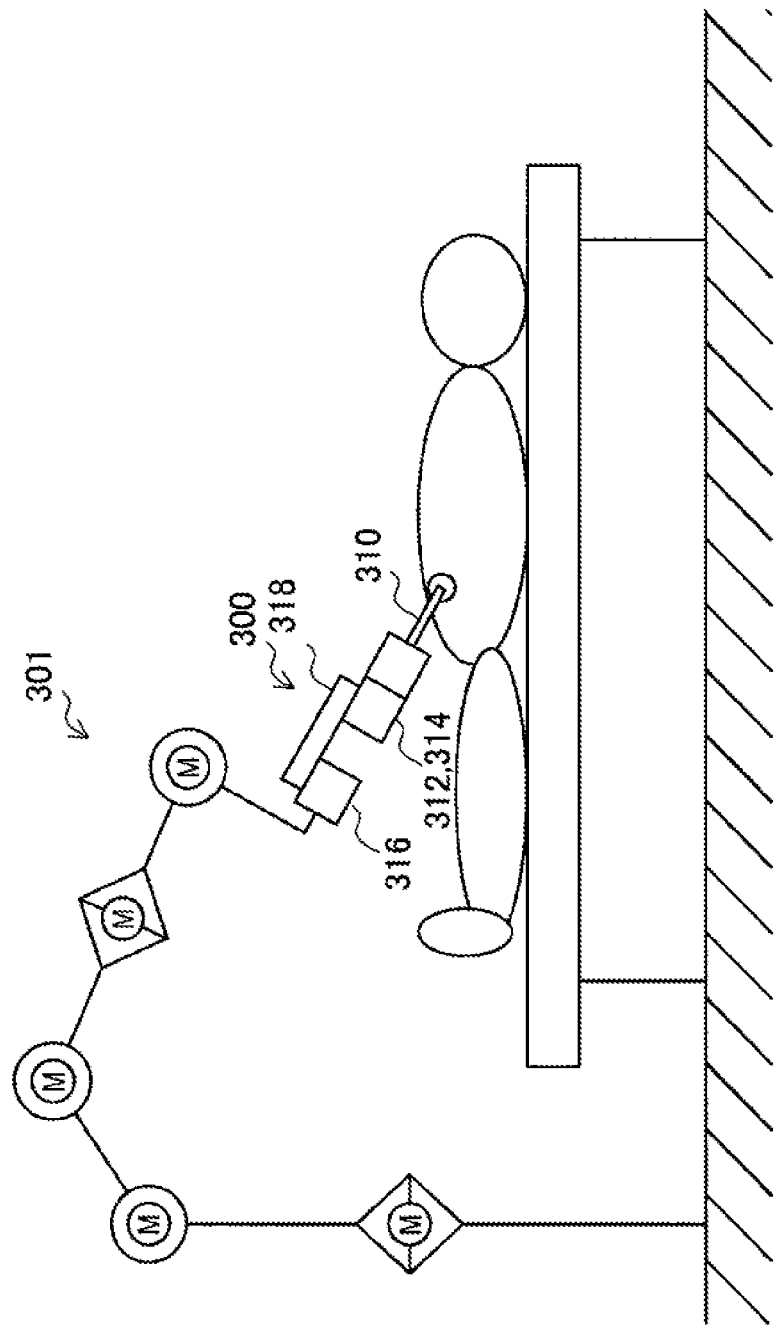
FIG. 13 is an explanatory diagram illustrating a use state of a jig holding apparatus according to a comparative example.

For comparison, FIG. 13 illustrates an endoscope observation apparatus 301 according to a reference example. A holding mechanism 300 of the endoscope observation apparatus 301 includes a rotation driving section 312 configured to cause an endoscope 310 to rotate about an axis while holding the endoscope 310, and a linear motion driving section 314 configured to cause the endoscope 310 to linearly move in an axial direction. A driving section 316 configured to drive the rotation driving section 312 and the linear motion driving section 314 is provided at a position spaced apart from the holding mechanism 300, and transmits a driving force to the rotation driving section 312 and the linear motion driving section 314 through a power transmission mechanism 318 including a belt, a pulley, or the like. Also, to facilitate understanding, the holding mechanism 300, the driving section 316, and the power transmission mechanism 318 are provided at a front end of a support arm apparatus having a configuration similar to that of the support arm apparatus illustrated in FIG. 12.

In the endoscope observation apparatus 301 according to the reference example, a size of a space in which the holding mechanism 300, the driving section 316, and the power transmission mechanism 318 are disposed is relatively increased. In contrast, in a case in which the jig holding apparatus 1 according to the present embodiment is used, since a power transmission mechanism is omitted and the driving section 110 is integrated with the holding mechanism 100, sizes of the driving section 110 and the holding mechanism 100 are reduced as a whole. Therefore, a workspace around the front end section of the jig holding apparatus 1 is expanded. Because of this, a surgeon, an assistant, or the like can easily perform work during surgery. Also, due to the expansion of the workspace, it is easy to secure a field of view of a surgeon, an assistant, or the like. Further, the expanded workspace may also be utilized as an arrangement space for other instruments used in surgery.

As described above, in the jig holding apparatus 1 according to the first embodiment, the lens tube 13 of the endoscope 10 is held by the holding section 173 provided inside the driving section 110 which includes the linear motion driving section 130 and the rotation driving section 150 including an ultrasonic motor. The linear motion driving section 130 and the rotation driving section 150 are disposed in series along an axial direction of the lens tube 13, i.e., the direction of linear motion by the linear motion driving section 130. In such a jig holding apparatus 1, since the holding mechanism 100 and the driving section 110 are integrated, the size of the holding mechanism 100 can be reduced. Also, since the endoscope 10 is held inside the driving section 110, a power transmission mechanism can be omitted and the size of the holding mechanism 100 can be reduced. Also, since each of the linear motion driving section 130 and the rotation driving section 150 includes an ultrasonic motor, a brake mechanism can be omitted and the size of the holding mechanism 100 can be reduced. In this way, a weight of the front end section of the jig holding apparatus 1 can be reduced, and a load to the actuator or the arm section can be reduced. Also, a space around the front end section of the jig holding apparatus 1 is expanded such that workability or operability is improved and it is easy to secure a field of view of surgeon or the like.

Also, in the jig holding apparatus 1 according to the present embodiment, the holding force of the endoscope 10 generated by the preload mechanisms 132 and 152 is set to a magnitude that allows the endoscope 10 to be detached by the user. Therefore, at the time of emergency such as when a failure has occurred in the support arm apparatus, the endoscope 10 can be promptly detached by the user's hand so that the endoscope 10 is drawn out from a body cavity of a patient.

Also, in the jig holding apparatus 1 according to the present embodiment, the holding section 173 holds the lens tube 13 of the endoscope 10 thorough the drape 108. Therefore, since the unclean area and the clean area are partitioned from each other, the endoscope 10 inserted into a body of a patient can be kept clean.

Also, in the jig holding apparatus 1 according to the present embodiment, the fixing member 18 including a metal material or disposable part is mounted at the lens tube 13 of the endoscope 10, and the holding section 173 holds the endoscope 10 through the fixing member 18. Therefore, at the time of using the endoscope 10, the lens tube 13 can be kept clean all the times.

Also, the jig holding apparatus 1 according to the present embodiment has the positioning mechanism for causing the endoscope 10 to be held at a predetermined position with respect to the holding mechanism 100. Therefore, adjustment of the position of the endoscope 10 can be performed with high precision by controlling the support arm apparatus.

3. Second Embodiment

Next, a configuration example of a jig holding apparatus according to a second embodiment of the present disclosure will be described in detail. In the jig holding apparatus according to the present embodiment, a linear motor is used instead of an ultrasonic motor as a linear motion driving section, and a direct-drive type electromagnetic motor is used instead of an ultrasonic motor as a rotation driving section. Hereinafter, a driving section 110 of the jig holding apparatus according to the present embodiment will be described mainly on the basis of differences from the driving section 110 according to the first embodiment.

Figure 14:
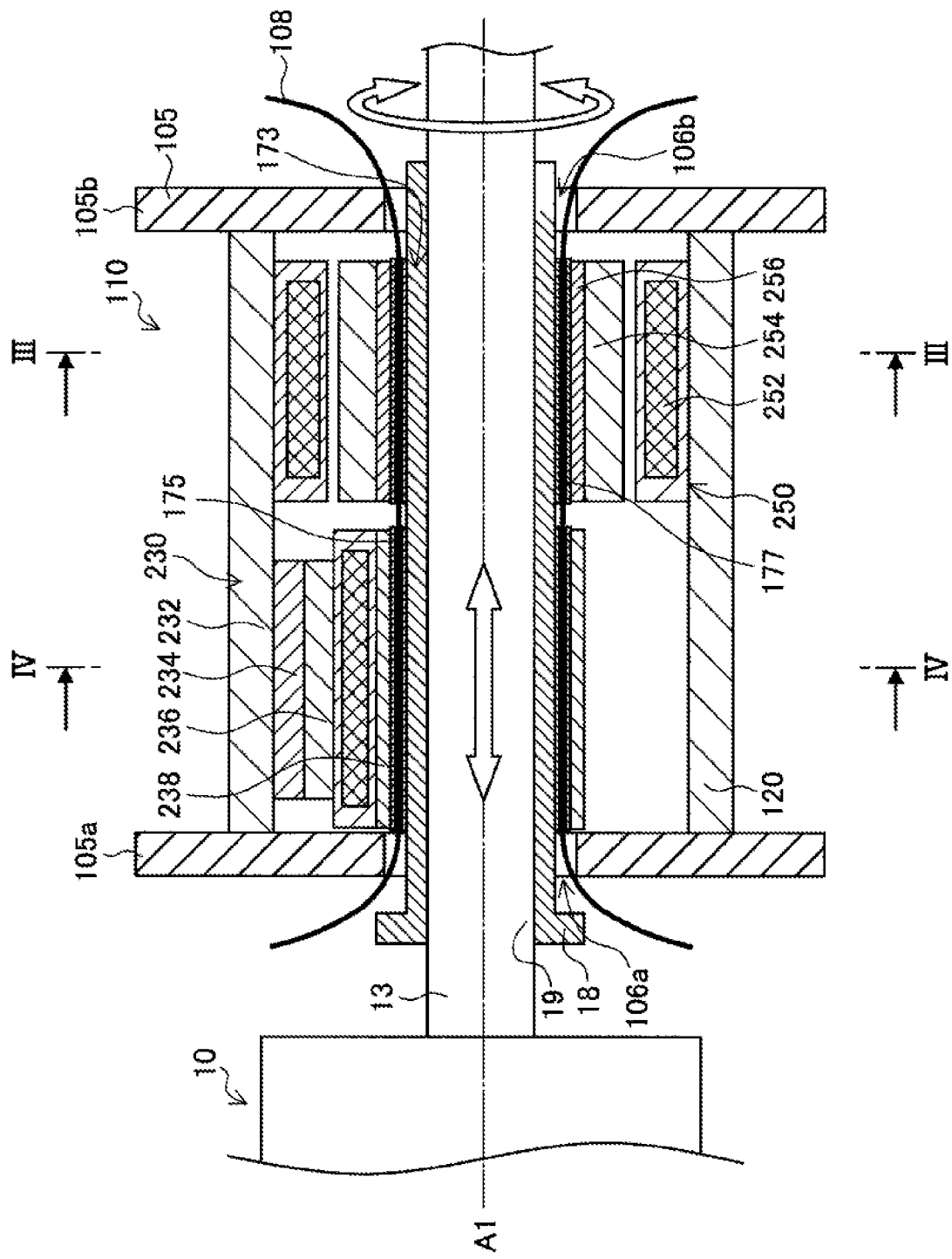
FIG. 14 is a cross-sectional diagram illustrating a configuration example of a holding mechanism of a jig holding apparatus according to a second embodiment of the present disclosure.
Figure 15:
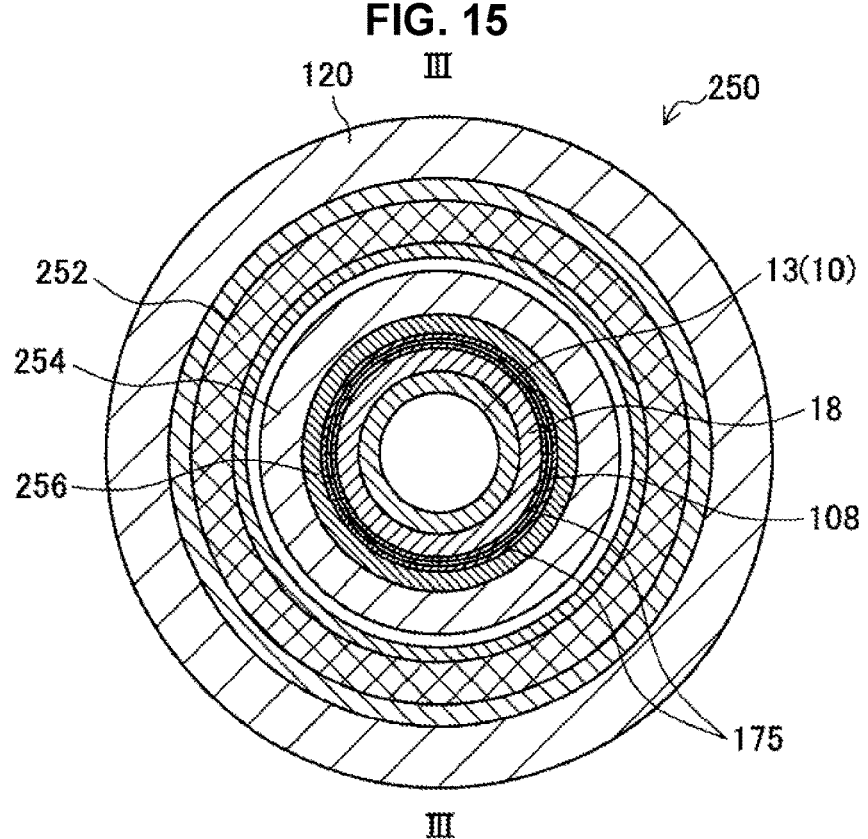
FIG. 15 is a cross-sectional diagram of a cross-section of the holding mechanism taken along line of FIG. 14.
Figure 16:
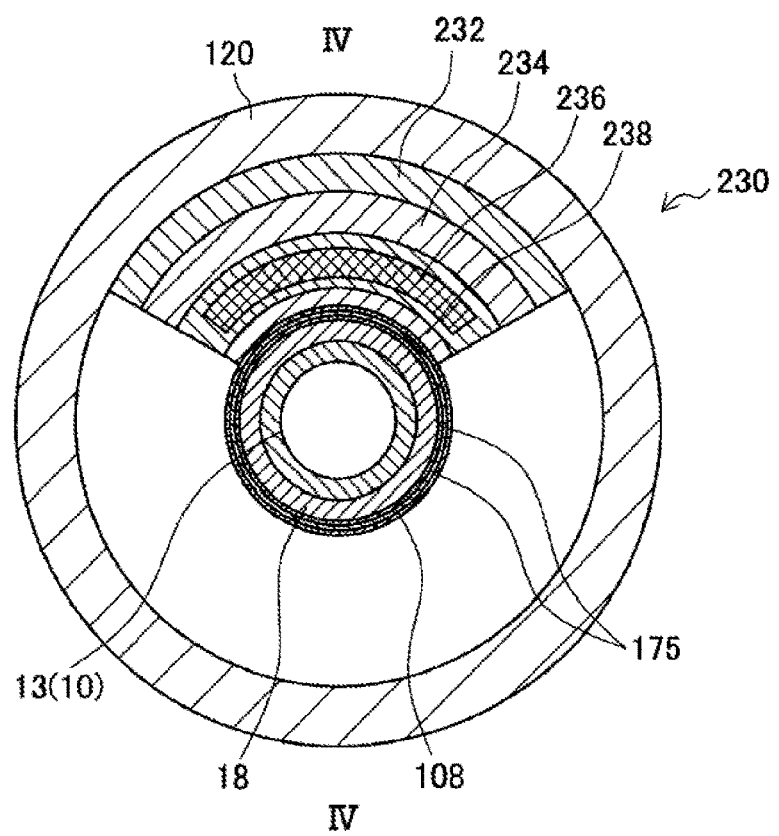
FIG. 16 is a cross-sectional diagram of a cross-section of the holding mechanism taken along line IV-IV of FIG. 14.

FIG. 14 is a schematic diagram illustrating a cross-section including the axis A1 in the holding mechanism 100 holding the endoscope 10. FIG. 16 is a schematic diagram illustrating a cross-section of the holding mechanism 100 taken along line of FIG. 14 in the holding mechanism 100 holding the endoscope 10, and FIG. 15 is a schematic diagram illustrating a cross-section of the holding mechanism 100 taken along line IV-IV of FIG. 14.

The driving section 110 of the holding mechanism 100 includes a rotation driving section 250 configured to cause the endoscope 10 rotate about the axis A1 and a linear motion driving section 230 configured to cause the endoscope 10 linearly move in the direction of the axis A1. The rotation driving section 250 and the linear motion driving section 230 are driven by a control command from the arm control apparatus 5045 so that the endoscope 10 is rotatable about the axis A1 and is linearly movable in the direction of the axis A1. Therefore, a capturing direction of the endoscope 10 is controlled by the driving section 110 with two degrees of freedom disposed to surround the lens tube 13.

The driving section 110 has the holding section 173 configured to hold the lens tube 13 of the endoscope 10 from a periphery thereof at the central section including the axis A1. The linear motion driving section 230 and the rotation driving section 250 are disposed around the held lens tube 13 of the endoscope 10. In the jig holding apparatus according to the present embodiment, the rotation driving section 250 is mostly in charge of a function of holding the lens tube 13 of the endoscope 10. For this reason, a hollow portion inside the rotation driving section 250 is configured as the holding section 173.

<3-1. Rotation Driving Section>

The rotation driving section 250 is configured using a direct-drive type electromagnetic motor. The rotation driving section 250 includes a magnet (permanent magnet) 254 as a mover, and a coil section 252 as a stator. The magnet 254 and the coil section 252 are provided in a substantially concentric shape about the axis A1, and the magnet 254 and the coil section 252 are disposed from the central side toward the outside in that order. As illustrated in FIG. 15, the magnet 254 and the coil section 252 are provided throughout an entire circumference of the axis A1.

The magnet 254 has a plurality of magnets in which a positive electrode and a negative electrode are disposed alternately in the circumferential direction. In addition, the coil section 252 has a plurality of coils arranged along the circumferential direction. A gap is provided between the magnet 254 and the coil section 252. The plurality of coils cause generation of a magnetic force of the positive electrode or the negative electrode on the magnet 254 side in accordance with a direction of a supplied current. Therefore, by varying magnetic poles of adjacent coils with respect to each coil of the coil section 252 and repeating changing of the magnetic poles of each coil, the magnet 254 rotates.

A first slider 256 is provided at an inner peripheral section of the magnet 254. The first slider 256 holds the fixing member 18 mounted at the lens tube 13 through the drape 108 clamped by the drape clamping body 177. Uneven sections which are fitted to each other are provided at abutting surfaces of the magnet 254 and the first slider 256. In the rotation driving section 250, the uneven sections are provided in parallel with the axis A1. Therefore, the magnet 254 and the first slider 256 are unable to rotate relative to each other in the circumferential direction, and in a case in which the magnet 254 rotates about the axis A1, the first slider 256 also rotates. On the other hand, in a case in which the endoscope 10 is caused to linearly move along the axis A1 by the linear motion driving section 230, relative movement between the first slider 256 and the magnet 254 is permitted in the direction of the uneven sections.

Note that in a case in which the rotation driving section 250 includes an electromagnetic motor, since a preload mechanism cannot be provided, the fixing member 18 and the first slider 256 may be caused to be engaged with each other by, for example, using the positioning mechanism configured to define the holding position of the endoscope 10. In this way, the endoscope 10 can be prevented from falling out of the holding mechanism 100.

<3-2. Linear Motion Driving Section>

The linear motion driving section 230 is configured using a linear motor. The linear motion driving section 230 includes a coil section 236 as a mover, a guide mechanism 234, and a magnet 232 as a stator. The coil section 236, the guide mechanism 234, and the magnet 232 are provided in a substantially concentric shape about the axis A1, and the coil section 236, the guide mechanism 234, and the magnet 232 are disposed from the central side toward the outside in that order. As illustrated in FIG. 16, the coil section 236, the guide mechanism 234, and the magnet 232 are provided in the range of 120° about the axis A1.

The magnet 232 has a plurality of magnets in which a positive electrode and a negative electrode are disposed alternately in the direction of the axis A1. In addition, the coil section 236 has a plurality of coils arranged in the direction of the axis A1. The plurality of coils cause generation of a magnetic force of the positive electrode or the negative electrode on the magnet 232 side in accordance with a direction of a supplied current. Therefore, by varying magnetic poles of adjacent coils with respect to each coil of the coil section 236 and repeating changing of the magnetic poles of each coil, the coil section 236 is moved along the axis A1.

The guide mechanism 234 has a function of guiding so that a moving direction of the coil section 236 is along the axis A1. For example, the guide mechanism 234 may have a rail section, which is in the direction of the axis A1, formed at a surface facing the coil section 236, and be fixed to the magnet 232. In this case, the coil section 236 has a guide groove fitted to the rail section, and by the guide groove moving along the rail section, the coil section 236 moves along the axis A1. Alternatively, the guide mechanism 234 may have a rail section, which is in the direction of the axis A1, at a surface facing the magnet 232, and be fixed to the coil section 236. In this case, the magnet 232 has a guide groove fitted to the rail section, and by the rail section moving along the guide groove, the coil section 236 is moved along the axis A1. Note that the positions at which the rail section and the guide groove are provided may also be reverse.

A second slider 238 is provided at an inner peripheral section of the coil section 236. The second slider 238 holds the fixing member 18 mounted at the lens tube 13 through the drape 108 clamped by the drape clamping body 177. Uneven sections which are fitted to each other are provided at abutting surfaces of the coil section 236 and the second slider 238. In the linear motion driving section 230, the uneven sections are provided along the circumferential direction. Therefore, in a case in which the coil section 236 is moved in the direction of the axis A1, the second slider 238 also moves. On the other hand, in a case in which the endoscope 10 is caused to rotate about the axis A1 by the rotation driving section 250, relative movement between the second slider 238 and the coil section 236 is permitted along the circumferential direction.

As described above, in the jig holding apparatus according to the second embodiment, the lens tube 13 of the endoscope 10 is held by the holding section 173 provided inside the driving section 110 which includes the linear motion driving section 230 including a linear motor and the rotation driving section 250 including an electromagnetic motor. The linear motion driving section 230 and the rotation driving section 250 are disposed in series along an axial direction of the lens tube 13, that is, a direction of linear motion by the linear motion driving section 230. Since the holding mechanism 100 and the driving section 110 are integrated in the jig holding apparatus 1, the size of the holding mechanisms 100 can be reduced. Also, since the endoscope 10 is held inside the driving section 110, a power transmission mechanism can be omitted, and the size of the holding mechanism 100 can be reduced. In this way, a weight of the front end section of the jig holding apparatus can be reduced, and a load to the actuator or the arm section can be reduced. Also, a space around the front end section of the jig holding apparatus 1 is expanded such that workability or operability is improved and it is easy to secure a field of view of surgeon or the like.

Also, in the jig holding apparatus according to the present embodiment, the holding section 173 holds the lens tube 13 of the endoscope 10 through the drape 108. Therefore, since the unclean area and the clean area are partitioned from each other, the endoscope 10 inserted into a body of a patient can be kept clean.

Also, in the jig holding apparatus 1 according to the present embodiment, the fixing member 18 including a metal material or disposable part is mounted at the lens tube 13 of the endoscope 10, and the holding section 173 holds the endoscope 10 through the fixing member 18. Therefore, at the time of using the endoscope 10, the lens tube 13 can be kept clean all the times.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure. Also, the configuration examples described in the above embodiments may be appropriately combined or substituted with each other.

For example, although a jig (endoscope) is caused to be held at the hollow portion of the rotation driving section of the holding mechanism 100 in the above embodiments, the present technology is not limited to such an example. For example, the linear motion driving section may be provided in a range that exceeds 180° about the axis A1, and a jig may be caused to be held at a hollow portion of the linear motion driving section. Alternatively, a jig may be caused to be held at hollow portions of both the linear motion driving section and the rotation driving section. In this case, a holding force which is caused to be generated by the preload mechanism may be set as a holding force that allows a jig to be detached by the user while the linear motion driving section and the rotation driving section are not driven.

In addition, although an endoscope is used as a jig to be caused to be held by the jig holding apparatus in the above embodiments, the present technology is not limited to such an example. For example, a jig to be held may include various jigs such as forceps and a retractor.

In addition, although the rotation driving section and the linear motion driving section include separate motors in the above embodiments, the present technology is not limited to such an example. For example, a rotation driving section and a linear motion driving section of a jig may be configured using a single ultrasonic motor. Likewise, a rotation driving section and a linear motion driving section of a jig may be configured using a single electromagnetic motor.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A jig holding apparatus including:
a holding mechanism including a holding section configured to detachably hold a predetermined jig from a periphery of the jig, and a linear motion driving section disposed around the jig held by the holding section and configured to cause the jig to linearly move.

(2)

The jig holding apparatus according to (1), in which the holding mechanism includes a rotation driving section disposed around the jig held by the holding section and configured to cause the jig to rotate about an axis which is oriented in a direction of the linear motion.

(3)

The jig holding apparatus according to (2), in which the linear motion driving section and the rotation driving section are disposed in series in the direction of the linear motion.

(4)

The jig holding apparatus according to any one of (1) to (3), in which the holding mechanism includes a preload mechanism configured to add a holding force when the jig is held by the holding section.

(5)

The jig holding apparatus according to (4), in which the holding force has a magnitude that allows the jig to be detached by a user while the linear motion driving section is not driven.

(6)

The jig holding apparatus according to any one of (1) to (5), in which the holding section holds the jig through a drape.

(7)

The jig holding apparatus according to any one of (1) to (6), including: a positioning mechanism configured to determine a holding position of the jig by the holding section.

(8)

The jig holding apparatus according to (7), in which the positioning mechanism includes a locking section provided at any one of an inner peripheral section of the holding section and an outer peripheral section of the jig, and an engaging section to which the locking section is lockable, the engaging section being provided at another of the inner peripheral section of the holding section and the outer peripheral section of the jig and.

(9)

The jig holding apparatus according to any one of (1) to (7), in which the holding section holds the jig through a fixing member mounted at the jig.

(10)

The jig holding apparatus according to (9), in which the fixing member includes a metal material.

(11)

The jig holding apparatus according to (9), in which the fixing member is detachable from the jig.

(12)

The jig holding apparatus according to any one of (9) to (11), including:
a positioning mechanism including a locking section provided at any one of an inner peripheral section of the holding section and an outer peripheral section of the fixing member, and an engaging section to which the locking section is lockable, the engaging section being provided at another of the inner peripheral section of the holding section and the outer peripheral section of the fixing member.

(13)

The jig holding apparatus according to any one of (1) to (12), in which the linear motion driving section is an ultrasonic motor.

(14)

The jig holding apparatus according to any one of (2) to (13), in which the rotation driving section is an ultrasonic motor.

(15)

The jig holding apparatus according to any one of (2) to (14), in which the linear motion driving section and the rotation driving section include a single ultrasonic motor.

(16)

The jig holding apparatus according to any one of (1) to (12), in which the linear motion driving section is a linear motor.

(17)

The jig holding apparatus according to any one of (1) to (13), in which the rotation driving section is an electromagnetic motor.

(18)

The jig holding apparatus according to any one of (1) to (17), in which the jig holding apparatus is a support arm apparatus including an arm section and a joint section, and a position of the jig is changed in accordance with a change in an attitude of the support arm apparatus.

(19)

A medical observation apparatus including:

a holding mechanism including an endoscope, a holding section configured to detachably hold the endoscope from a periphery of the endoscope, and a linear motion driving section provided around the endoscope held by the holding section and configured to cause the endoscope to linearly move.

REFERENCE SIGNS LIST 1 jig holding apparatus (support arm apparatus)
10 endoscope (jig)
13 lens tube
18 fixing member
100 holding mechanism
105 holding case
108 drape
110 driving section
130 linear motion driving section (ultrasonic motor)
132 preload mechanism
134 piezoelectric body
135 metallic body
136 stator
138 mover
150 rotation driving section (ultrasonic motor)
152 preload mechanism
154 piezoelectric body
155 metallic body
156 stator
158 mover
173 holding section

The invention claimed is:

1. A jig holding apparatus comprising:
   a holding assembly including a holder configured to detachably hold a predetermined jig from a periphery of the jig, and a linear motion driver disposed around the jig held by the holder and configured to cause the jig to linearly move,
   wherein the linear motion driver includes a mover and a stator having a piezoelectric body and a metallic body, the piezoelectric, body includes a plurality of piezoelectric sub-bodies divided in a direction of an axis of the jig, the metallic body has a comb-tooth shape having comb teeth divided in the direction of the axis of the jig, and each of the piezoelectric sub-bodies corresponds to one of the comb teeth.

2. The jig holding apparatus according to claim 1, wherein the holding assembly further includes a rotation driver disposed around the jig held by the holder and configured to cause the jig to rotate about an axis which is oriented in a direction of the linear motion.

3. The jig holding apparatus according to claim 2, wherein the linear motion driver and the rotation driver are disposed in series in the direction of the linear motion.

4. The jig holding apparatus according to claim 2, wherein the rotation driver is an ultrasonic motor.

5. The jig holding apparatus according to claim 2, wherein the linear motion driver and the rotation driver include a single ultrasonic motor.

6. The jig holding apparatus according to claim 1, wherein the holding assembly further includes a preloader configured to add a holding force when the jig is held by the holder, the preloader is disposed in a concentric shape at an outside of the stator.

7. The jig holding apparatus according to claim 6, wherein the holding force has a magnitude that allows the jig to be detached by a user.

8. The jig holding apparatus according to claim 6, wherein the mover, the stator, and the preloader are provided in a range of 120° about the axis of the jig.

9. The jig holding apparatus according to claim 1, wherein the holder holds the jig through a drape.

10. The jig holding apparatus according to claim 1, comprising:
    a positioner configured to determine a holding position of the jig by the holder.

11. The jig holding apparatus according to claim 10, wherein the positioner includes a locker provided at any one of an inner peripheral section of the holder and an outer peripheral section of the jig, and an engager to which the locker is lockable, the engager being provided at another of the inner peripheral section of the holder and the outer peripheral section of the jig.

12. The jig holding apparatus according to claim 1, wherein the holder holds the jig through a fixer mounted at the jig.

13. The jig holding apparatus according to claim 12, wherein the fixer includes a metal material.

14. The jig holding apparatus according to claim 12, wherein the fixer is detachable from the jig.

15. The jig holding apparatus according to claim 12, comprising:
    a positioner including a locker provided at any one of an inner peripheral section of the holder and an outer peripheral section of the fixer, and an engager to which the locker is lockable, the engager being provided at another of the inner peripheral section of the holder and the outer peripheral section of the fixer.

16. The jig holding apparatus according to claim 1, wherein the linear motion driver is an ultrasonic motor.

17. The jig holding apparatus according to claim 1,
    wherein the jig holding apparatus is a support arm apparatus including an arm and a joint, and
    a position of the jig is changed in accordance with a change in an attitude of the support arm apparatus.

18. A medical observation apparatus comprising:
    a holding assembly including an endoscope, a holder configured to detachably hold the endoscope from a periphery of the endoscope, and a linear motion driver provided around the endoscope held by the holder and configured to cause the endoscope to linearly move;

wherein the linear motion driver includes a mover and a stator having a piezoelectric body and a metallic body, the piezoelectric body includes a plurality of piezoelectric sub-bodies divided in a direction of an axis of the endoscope, the metallic body has a comb-tooth shape having comb teeth divided in the direction of the axis of the endoscope, and each of the piezoelectric sub-bodies corresponds to one of the comb teeth.

* * * * *